United States Patent [19]

Hübsch et al.

[11] Patent Number: 5,075,311
[45] Date of Patent: Dec. 24, 1991

[54] HMG-COA REDUCTASE INHIBITING SUBSTITUTED PRYIDO (2,3-D) PYRIMIDINES

[75] Inventors: Walter Hübsch; Rolf Angerbauer; Peter Fey, all of Wuppertal; Thomas Philipps, Cologne; Hilmar Bischoff, Wuppertal; Dieter Petzinna, Duesseldorf; Delf Schmidt, Wuppertal, all of Fed. Rep. of Germany; Günter Thomas, Arese, Italy

[73] Assignee: Bayer Aktiengesellschaft, Leverkusen, Fed. Rep. of Germany

[21] Appl. No.: 460,212

[22] Filed: Jan. 2, 1990

[30] Foreign Application Priority Data

Jan. 7, 1989 [DE] Fed. Rep. of Germany ....... 3900363
Jul. 18, 1989 [IT] Italy ................. 21215A/89

[51] Int. Cl.$^5$ .................. A61K 31/505; C07D 471/02
[52] U.S. Cl. ..................................... 514/258; 544/279
[58] Field of Search ........................ 544/279; 514/258

[56] References Cited

U.S. PATENT DOCUMENTS 4,231,938 11/1980 Monaghan et al. ................. 549/292
4,613,610 9/1986 Wareing ................................. 54/406
4,761,419 8/1988 Picaradi et al. ..................... 514/311

FOREIGN PATENT DOCUMENTS 0022478 2/1983 European Pat. Off.
0114027 7/1984 Fed. Rep. of Germany.

Primary Examiner—Mukund J. Shah
Assistant Examiner—Jyothsna Venkat
Attorney, Agent, or Firm—Sprung, Horn, Kramer & Woods

[57] ABSTRACT

New substituted pyrido(2,3-d)pyrimidines of the formula

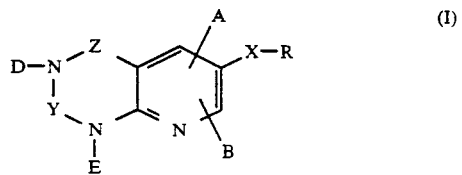

can be prepared by reduction of corresponding pyrido(2,3-d)-pyrimidines which are substituted by a ketone radical, and subsequent hydrolysis, cyclization or hydrogenation. The new compounds can be used to inhibit HMG-CoA reductase.

12 Claims, No Drawings

HMG-COA REDUCTASE INHIBITING SUBSTITUTED PRYIDO (2,3-D) PYRIMIDINES

The invention relates to new substituted pyrido(2,3-d)pyrimidines, and to intermediates for their preparation, their preparation and their use in medicaments.

It is known that lactone derivatives isolated from fungal cultures are inhibitors of 3-hydroxy-3-methyl-glutaryl-coenzyme A reductase (HMG-CoA reductase) [mevinolin, EP-A 22,478; U.S. Pat. No. 4,231,938]. Moreover, certain indole derivatives or pyrazole derivatives are inhibitors of HMG-CoA reductase [EP-A 1,114,027; U.S. Pat. No. 4,613,610].

New substituted pyrido(2,3-d)pyrimidines of the general formula (I)

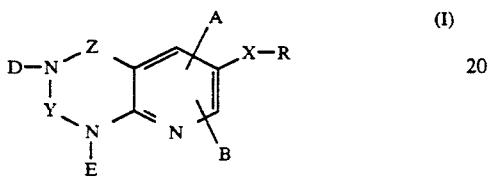

in which

A - represents a 5- to 7-membered heterocycle which may contain up to 4 heteroatoms from the series comprising sulphur, oxygen or nitrogen and which is optionally monosubstituted to trisubstituted by identical or different substituents from the series comprising halogen, hydroxyl, trifluoromethyl, straight-chain or branched alkyl, alkoxy or alkoxycarbonyl each having up to 8 carbon atoms, aryl having 6 to 10 carbon atoms or by a group of the formula $-NR^1R^2$, in which R$^1$ and R$^2$ are identical or different and denotes hydrogen, aryl or arylsulphonyl having 6 to 10 carbon atoms or straight-chain or branched alkyl or alkylsulphonyl having up to 8 carbon atoms, where the last-mentioned radicals are optionally substituted by aryl having 6 to 10 carbon atoms, or denote a group of the formula $-COR^3$, in which R$^3$ - denotes straight-chain or branched alkyl or alkoxy having up to 8 carbon atoms or phenyl, represents aryl having 6 to 10 carbon atoms, which is optionally monosubstituted to pentasubstituted by identical or different substituents from the series comprising straight-chain or branched alkyl, alkylthio, alkylsulphonyl, alkoxy or alkoxycarbonyl each having up to 10 carbon atoms, which may in turn be substituted by trifluoromethyl, hydroxyl, alkoxy having up to 6 carbon atoms, phenyl or phenoxy, or is substituted by aryl, aryloxy, arylthio or arylsulphonyl having 6 to 10 carbon atoms, or by halogen, nitro, cyano, trifluoromethyl, benzyloxy or a group of the formula $-NR^1R^2$, in which R$^1$ and R$^2$ have the abovementioned meanings, or represents straight-chain or branched alkyl, each having up to 8 carbon atoms B - represents cycloalkyl having 3 to 8 carbon atoms, represents trifluoromethyl or straight-chain or branched alkyl having up to 12 carbon atoms, which is optionally substituted by halogen, hydroxyl, cyano, azido, trifluoromethyl, alkylthio, alkylsulphonyl or alkoxy each having up to 8 carbon atoms or by aryl, aryloxy or arylthio having 6 to 10 carbon atoms, where the aryl radicals may optionally be monosubstituted to trisubstituted by identical or different substituents from the series comprising halogen, cyano, trifluoromethyl, trifluoromethoxy, straight-chain or branched alkyl, alkoxy, alkylthio or alkylsulphonyl each having up to 8 carbon atoms, or is substituted by a group of the formula $-NR^1R^2$ or $-COR^3$, in which R$^1$, R$^2$ and R$^3$ have the abovementioned meanings, represents aryl having 6 to 10 carbon atoms, which is optionally substituted by halogen, cyano, nitro, trifluoromethyl, straight-chain or branched alkyl, alkoxy or alkoxycarbonyl each having up to 8 carbon atoms or amino, D - represents hydrogen, hydroxyl or cycloalkyl having 3 to 8 carbon atoms represents straight-chain or branched alkyl each having up to 12 carbon atoms, which is optionally substituted by halogen, hydroxyl or alkoxy having up to 8 carbon atoms, E - has the meaning mentioned above for A and is identical or different to this, or represents hydrogen or represents cycloalkyl having 3 to 8 carbon atoms, represents straight-chain or branched alkyl having up to 12 carbon atoms, which is optionally substituted by halogen, straight-chain or branched alkenyl having up to 8 carbon atoms, aryl having 6 to 10 carbon atoms, by a 5- to 7-membered heterocycle having up to 4 heteroatoms from the series comprising nitrogen, oxygen or sulphur or by a group of the formula $-NR^1R^2$, $-OR^4$, $-COR^5$ or $-S(O)_n-R^6$, in which R$^1$ and R$^2$ have the abovementioned meanings, R$^4$ - denotes hydrogen or straight-chain or branched alkyl having up to 10 carbon atoms, which is optionally substituted by hydroxyl, trialkylsilyl having up to 10 carbon atoms in the alkyl moiety, or halogen or aryl having 6 to 10 carbon atoms, denotes trialkylsilyl having up to 10 carbon atoms or cycloalkyl having 3 to 8 carbon atoms or aryl having 6 to 10 carbon atoms, which may in turn be substituted by halogen, cyano, nitro or amino, or denotes a group of the formula $-COR^7$, in which R$^7$ - denotes straight-chain or branched alkyl having up to 8 carbon atoms, aryl having 6 to 10 carbon atoms or the group $-NR^1R^2$, in which R$^1$ and R$^2$ have the abovementioned meanings, R$^5$ - denotes hydrogen or straight-chain or branched alkyl having up to 8 carbon atoms, which is optionally substituted by hydroxyl, phenyl, halogen or cyano, denotes aryl having 6 to 10 carbon atoms, which may be substituted by halogen, amino, hydroxyl, nitro or cyano, or denotes a group of the formula $-NR^1R^2$ or $-OR^4$, in which R$^1$, R$^2$ and R$^4$ have the abovementioned meanings, n - denotes a number 0 or 2, R⁶ - denotes straight-chain or branched alkyl having up to 10 carbon atoms, in which may be substituted by halogen, hydroxyl, phenyl or a group of the formula —NR¹R², in which
R¹ and R² have the abovementioned meanings,
denotes aryl having 6 to 10 carbon atoms, which may be substituted by halogen, hydroxyl, cyano, nitro or amino, or
denotes a group of the formula —NR¹R², if n represents the number 2, in which
R¹ and R² have the abovementioned meanings,
or
E - represents a group of the formula —NR¹R² or —OR⁴, in which
R¹, R² and R⁴ have the abovementioned meanings,
Y and Z are identical or different and represent a group of the formula

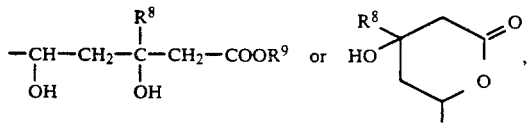

or
Y - represents a thiocarbonyl group,
X - represents a group of the formula —CH₂—CH₂— or —CH=CH—, and
R - represents a group of the formula

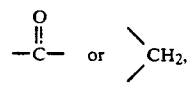

in which
R⁸ - denotes hydrogen or straight-chain or branched alkyl having up to 10 carbon atoms, and
R⁹ - denotes hydrogen or straight-chain or branched alkyl having up to 10 carbon atoms, which may be substituted by phenyl, or
denotes aryl having 6 to 10 carbon atoms or a cation,
and their salts have now been found.

If R⁹ forms an ester radical with the carboxy group, then a physiologically tolerable ester radical, which is easily hydrolyzed in vivo to give a free carboxy group and a corresponding physiologically tolerable alcohol, is preferably meant by this. These include, for example, alkyl esters (C₁ to C₆) and aryl esters (C₇ to C₁₀), preferably (C₁-C₄)-alkyl esters and benzyl esters. Moreover, the following ester radicals may be mentioned: methyl esters, ethyl esters, propyl esters and benzyl esters.

If R⁹ represents a cation, then a physiologically tolerable metal cation or ammonium cation is preferably meant. Preferred cations in this connection are alkali metal or alkaline earth metal cations such as, for example, sodium, potassium, magnesium or calcium cations, and also aluminum or ammonium cations, and non-toxic substituted ammonium cations of amines such as (C₁-C₄)-dialkylamines, (C₁-C₄)-trialkylamines, procaine, dibenzylamine, N,N'-dibenzylethylenediamine, N-benzyl-β-phenylethylamine, N-methylmorpholine or N-ethylmorpholine, 1-ephenamine, dihydroabietylamine, N,N'-bis-dihydroabietylethylenediamine, N-lower alkylpiperidine and other amines which may be used for the formation of salts.

Surprisingly, the substituted pyrido(2,3-d)pyrimidines according to the invention show a superior inhibitory action on HMG-CoA reductase (3-hydroxy-3-methyl-glutaryl-coenzyme A reductase).

In the context of the general formula (I), compounds of the general formula (Ia) and (Ib)

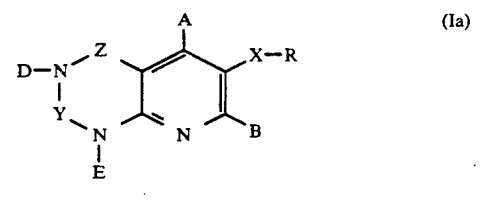

and

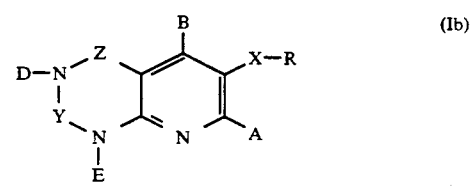

in which
A, B, D, E, X, Y, Z and R have the abovementioned meanings, are preferred.

Preferred compounds are those of the general formula (Ia) and (Ib), in which
A - represents thienyl, furyl, pyridyl or pyrimidyl, each of which is optionally monosubstituted to trisubstituted by identical or different substituents from the series comprising fluorine, chlorine, bromine, hydroxyl, trifluoromethyl, straight-chain or branched alkyl, alkoxy or alkoxycarbonyl each having up to 6 carbon atoms, phenyl, or by a group of the formula —NR¹R², in which
R¹ and R² are identical or different and
denote hydrogen, phenyl, phenylsulphonyl, straight-chain or branched alkyl or alkylsulphonyl having up to 6 carbon atoms, or benzyl or benzylsulphonyl,
denote a group of the formula —COR³, in which
R³ -denotes straight-chain or branched alkyl or alkoxy having up to 6 carbon atoms or phenyl, or
represents phenyl or naphthyl, which is optionally monosubstituted to tetrasubstituted by identical or different straight-chain or branched substituents from the series comprising alkyl, alkoxy or alkoxycarbonyl each having up to 8 carbon atoms, which may in turn be substituted by trifluoromethyl, hydroxyl, alkoxyl having up to 4 carbon atoms, phenyl or phenoxy, or is substituted by phenyl, phenoxy, phenylthio, phenylsulphonyl, fluorine, chlorine, bromine, nitro, cyano, trifluoromethyl, benzyloxy or by a group of the formula —NR¹R², in which
R¹ and R² have the abovementioned meanings, or represents straight-chain or branched alkyl each having up to 6 carbon atoms
B - represents cyclopropyl, cyclobutyl, cyclopentyl or cyclohexyl,
represents trifluoromethyl or straight-chain or branched alkyl having up to 10 carbon atoms, which is optionally substituted by fluorine, chlorine, bromine, hydroxyl, cyano, azido, trifluoromethyl, methylthio, methylsulphonyl, alkoxy having up to 6 carbon atoms or by phenyl, phenyloxy or phenylthio, where the phenyl radicals may be monosubstituted or disubstituted by identical or different substituents from the series comprising fluorine, chlorine, bromine, cyano, trifluoromethyl, trifluoromethoxy, straight-chain or branched alkyl, alkoxy, alkylthio or alkylsulphonyl each having up to 6 carbon atoms, or is substituted by a group of the formula —$NR^1R^2$ or —$COR^3$, in which $R^1$, $R^2$ and $R^3$ have the abovementioned meanings, or represents phenyl, which is optionally substituted by fluorine or chlorine, D - represents hydrogen, hydroxyl or represents cyclopropyl, cyclobutyl, cyclopentyl or cyclohexyl, represents straight-chain or branched alkyl having up to 10 carbon atoms, which is optionally substituted by fluorine, chlorine, bromine, hydroxyl or alkoxy having up to 6 carbon atoms, E - has the meaning mentioned above for A and is identical or different to this, or represents hydrogen or represents cyclopropyl, cyclobutyl, cyclopentyl or cyclohexyl, represents straight-chain or branched alkyl having up to 10 carbon atoms, which is optionally substituted by fluorine, chlorine, bromine, straight-chain or branched alkenyl having up to 6 carbon atoms, phenyl, pyrimidyl, pyrrolyl, pyrrolidinyl, furyl or thiazolyl, or by a group of the formula —$NR^1R^2$, —$OR^4$, —$COR^5$ or —$S(O)_n$—$R^6$, in which $R^1$ and $R^2$ have the abovementioned meanings, $R^4$ - denotes hydrogen or straight-chain or branched alkyl having up to 8 carbon atoms, which is optionally substituted by hydroxyl, fluorine, chorine, bromine or by phenyl, or denotes a group of the formula —$COR^7$, in which $R^7$ - denotes straight-chain or branched alkyl having up to 6 carbon atoms, phenyl or a group of the formula —$NR^1R^2$, in which $R^1$ and $R^2$ have the abovementioned meanings, $R^5$ - denotes hydrogen, or straight-chain or branched alkyl having up to 6 carbon atoms, which is optionally substituted by hydroxyl, phenyl, fluorine, chlorine, bromine or cyano, denotes phenyl which may in turn be substituted by fluorine, chlorine, bromine, amino, hydroxyl, nitro or cyano, or denotes a group of the formula —$NR^1R^2$ or —$OR^4$, in which $R^1$, $R^2$ and $R^4$ have the abovementioned meanings, n - denotes a number 0 or 2, $R^6$ - denotes straight-chain or branched alkyl having up to 8 carbon atoms or, phenyl which may be substituted by fluorine, chlorine, bromine, hydroxyl, cyano, nitro or amino, or may denote a group of the formula —$NR^1R^2$, if n represents the number 2, in which $R^1$ and $R^2$ have the abovementioned meanings, or E - represents a group of the formula —$NR^1R^2$ or —$OR^4$, in which $R^1$, $R^2$ and $R^4$ have the abovementioned meanings, Y and Z are identical or different and represent a group of the formula

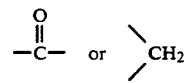

or

Y - represents a thiocarbonyl group,

X - represents a group of the formula —$CH_2$—$CH_2$— or —CH=CH— and

R - represents a group of the formula

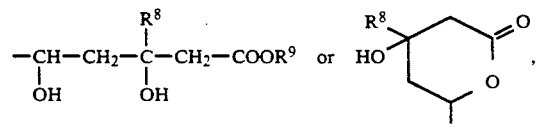

in which $R^8$ - denotes hydrogen or straight-chain or branched alkyl having up to 8 carbon atoms, and $R^9$ - denotes hydrogen or straight-chain or branched alkyl having up to 8 carbon atoms or benzyl, or denotes phenyl or a cation and their salts.

Particularly preferred compounds are those of the general formulae (Ia) and (Ib), in which A - represents thienyl, furyl or pyridyl, which is optionally monosubstituted or disubstituted by identical or different substituents from the series comprising fluorine, chlorine, bromine, hydroxyl, trifluoromethyl, methyl, ethyl, methoxy, ethoxy or phenyl, or by a group of the formula —$NR^1R^2$, in which $R^1$ and $R^2$ are identical or different and denote hydrogen, phenyl, or straight-chain or branched alkyl having up to 4 carbon atoms, represents phenyl which is optionally monosubstituted to trisubstituted by identical or different substituents from the series comprising straight-chain or branched alkyl or alkoxy each having up to 6 carbon atoms, which may in turn be substituted by trifluoromethyl, hydroxyl, methoxy, ethoxy, propoxy, phenyl or phenoxy, or is substituted by phenyl, phenoxy, fluorine or chlorine, or represents straight-chain or branched alkyl having up to 4 carbon atoms B - represents cyclopropyl, cyclobutyl, cyclopentyl or cyclohexyl, represents methyl, ethyl, propyl, isopropyl, butyl, tert. butyl or trifluoromethyl, represents phenyl, which is optionally substituted by fluorine, D - represents hydrogen or
represents cyclopropyl, cyclopentyl or cyclohexyl,
represents methyl, ethyl, propyl, isopropyl, butyl or tert. butyl, E - has the meaning mentioned above for A and is identical or different to this, or
represents hydrogen, or
represents cyclopropyl, cyclopentyl or cyclohexyl,
represents straight-chain or branched alkyl having up to 8 carbon atoms, which is optionally substituted by fluorine, chlorine, straight-chain or branched alkenyl having up to 4 carbon atoms, phenyl or furyl, or
is substituted by a group of the formula —NR¹R² or —OR⁴, in which
R¹ and R² have the abovementioned meanings,
R⁴ - denotes hydrogen or
straight-chain or branched alkyl having up to 6 carbon atoms, which is optionally substituted by hydroxyl or by phenyl, or E - represents a group of the formula —NR¹R², in which
R¹ and R² have the abovementioned meanings, Y and Z are identical or different and represent a group of the formula

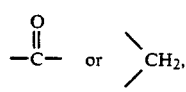

or

Y - represents a thiocarbonyl group,
X - represents a group —CH=CH— and
R - represents a group of the formula

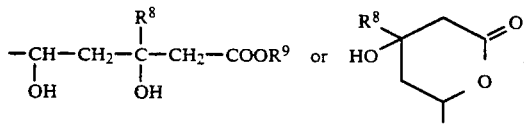

in which
R⁸ - denotes hydrogen, methyl, ethyl, propyl, isopropyl, butyl, isobutyl or tert. butyl and p2 R⁹ - denotes hydrogen, methyl, ethyl, propyl, isopropyl, butyl, isobutyl, tert. butyl or benzyl, or
denotes a sodium, potassium, calcium, magnesium or ammonium ion,
and their salts.

The substituted pyrido(2,3-d)pyrimidines of the general formula (I) according to the invention have several asymmetric carbon atoms and can therefore exist in various stereochemical forms. The invention relates both to the individual isomers and to their mixtures.

Depending on the meaning of the group X or the radical R, different stereoisomers result, which are intended to be illustrated in more detail in the following:

a) if the group -X- represents a group of the formula —CH=CH—, the compounds according to the invention can exist in two stereoisomeric forms which can have the E configuration (II) or Z configuration (III) on the double bond:

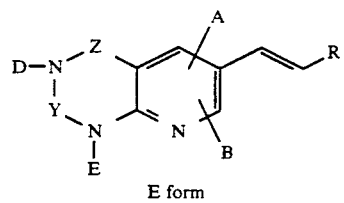

E form

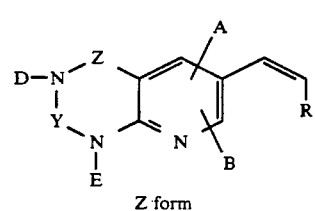

Z form (A, B, D, E, Y, Z and R have the abovementioned meanings).

Preferred compounds of the general formula (I) are those which have the E configuration (II).

b) If the radical -R- represents a group of the formula

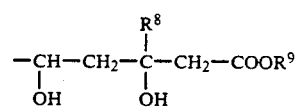

the compounds of the general formula (I) have at least two asymmetric carbon atoms, namely the two carbon atoms to which the hydroxyl groups are bonded. Depending on the relative position of these hydroxyl groups to one another, the compounds according to the invention may be present in the erythro configuration (IV) or in the threo configuration (V).

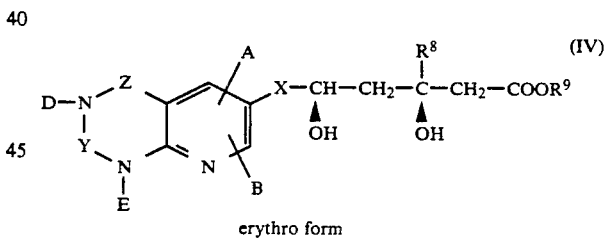

erythro form

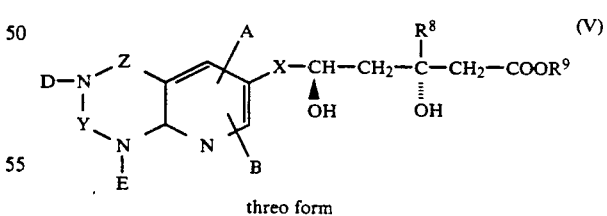

threo form

In turn, two enantiomers each exist both of the compounds in the erythro and in the threo configuration, namely the 3R,5S-isomer or the 3S,5R-isomer (erythro form) and the 3R,5R-isomer and 3S,5S-isomer (threo form).

In this connection, the isomers in the erythro configuration are preferred, particularly preferably the 3R,5S-isomer and the 3R,5S-3S,5R-racemate.

c) If the radical -R- represents a group of the formula

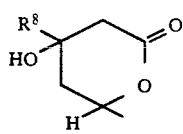

the substituted pyrido(2,3-d)pyrimidines have at least two asymmetric carbon atoms, namely the carbon atom to which the hydroxyl group is bonded, and the carbon atom to which the radical of the formula

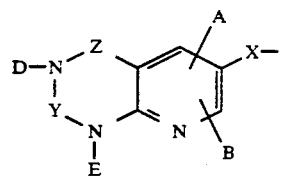

is bonded. Depending on the position of the hydroxyl group to the free valency on the lactone ring, the substituted pyrido(2,3-d)pyrimidines may be present as cis-lactones (VI) or as trans-lactones (VII).

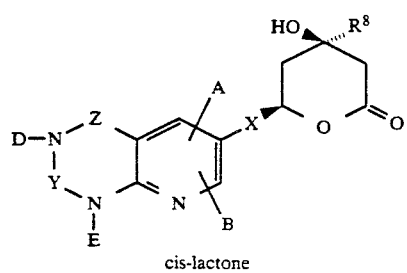

cis-lactone (VI)

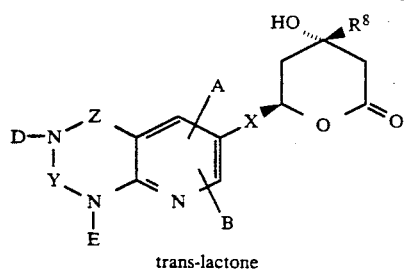

trans-lactone (VII)

In turn, two isomers each exist of the cis-lactone and the trans-lactone, namely the 4R,6R-isomer or the 4S,6S-isomer (cis-lactone), and the 4R,6S-isomer or 4S,6R-isomer (trans-lactone). Preferred isomers are the trans-lactones. The 4R,6S-isomer (trans) and the 4R,6S-4S,6R-racemate are particularly preferred in this connection.

For example, the following isomeric forms of the substituted pyrido(2,3-d)pyrimidines may be mentioned:

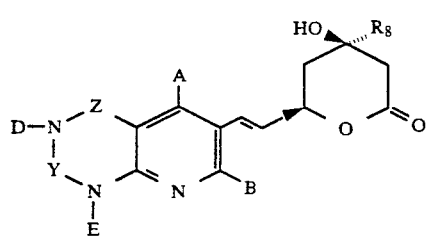

-continued

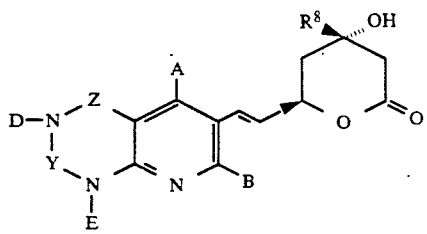

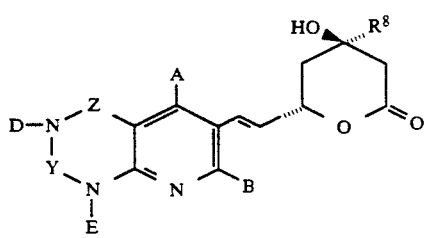

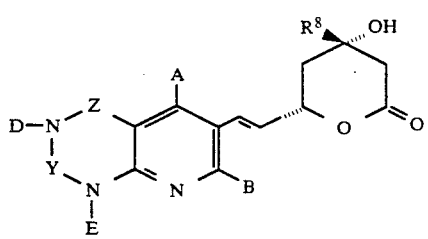

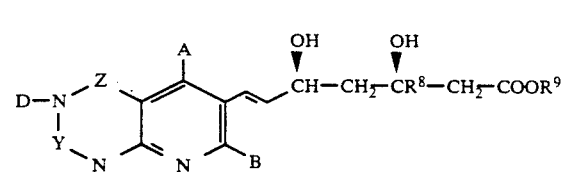

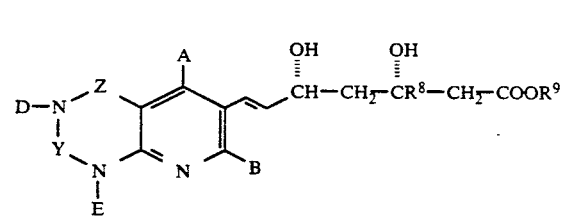

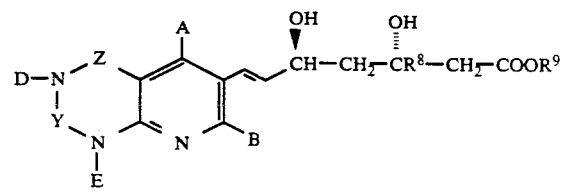

-continued

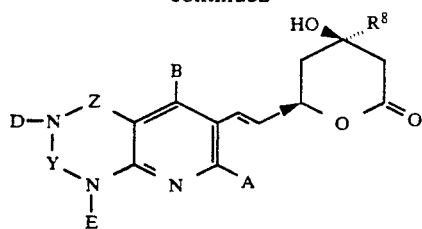

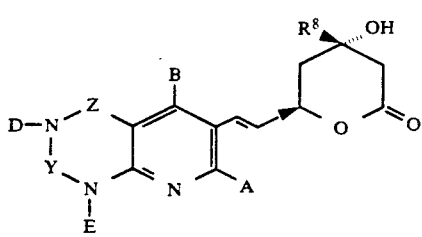

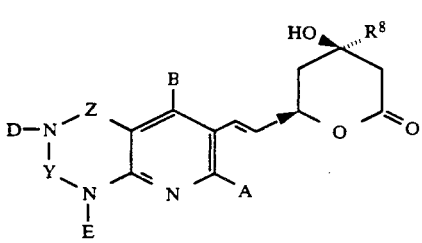

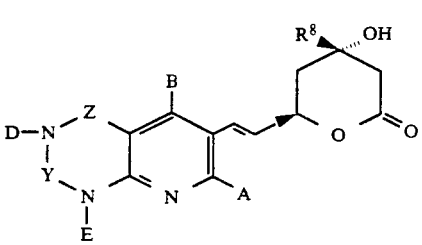

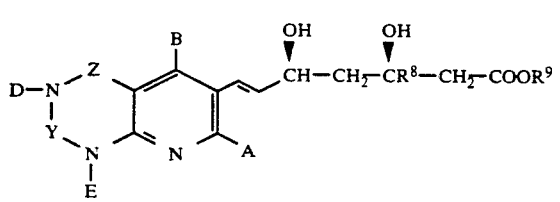

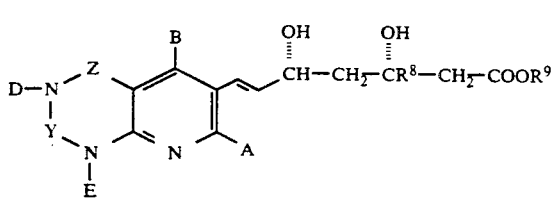

-continued

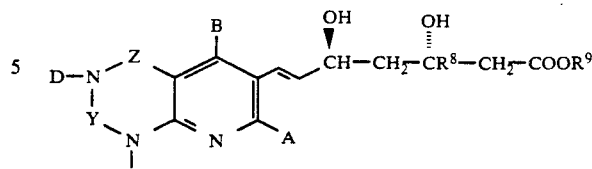

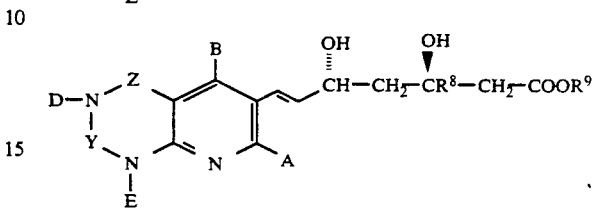

In addition, a process for the preparation of the substituted pyrido(2,3-d)pyrimidines of the general formula (I)

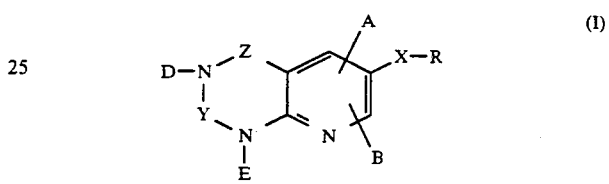

in which
A, B, D, E, X, Y, Z and R have the abovementioned meanings,
has been found which is characterized in that ketones of the general formula (VIII)

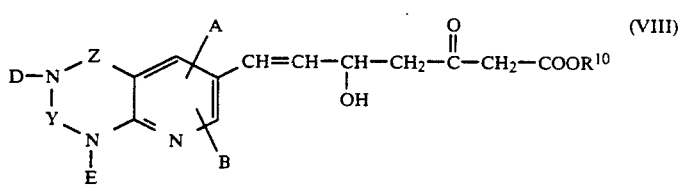

in which
A, B, D, E, Y and Z have the abovementioned meanings, and
$R^{10}$ - represents alkyl having up to 6 carbon atoms,
are reduced,
in the case of the preparation of the acids the esters are hydrolyzed,
in the case of the preparation of the lactones the carboxylic acids are cyclized,
in the case of the preparation of the salts either the esters or the lactones are hydrolyzed,
in the case of the preparation of the ethylene compounds (X=—CH$_2$—CH$_2$—) the ethene compounds (X=—CH=CH—) are hydrogenated according to customary methods, and, if appropriate, isomers are separated.

The process according to the invention can be illustrated by the following equation:

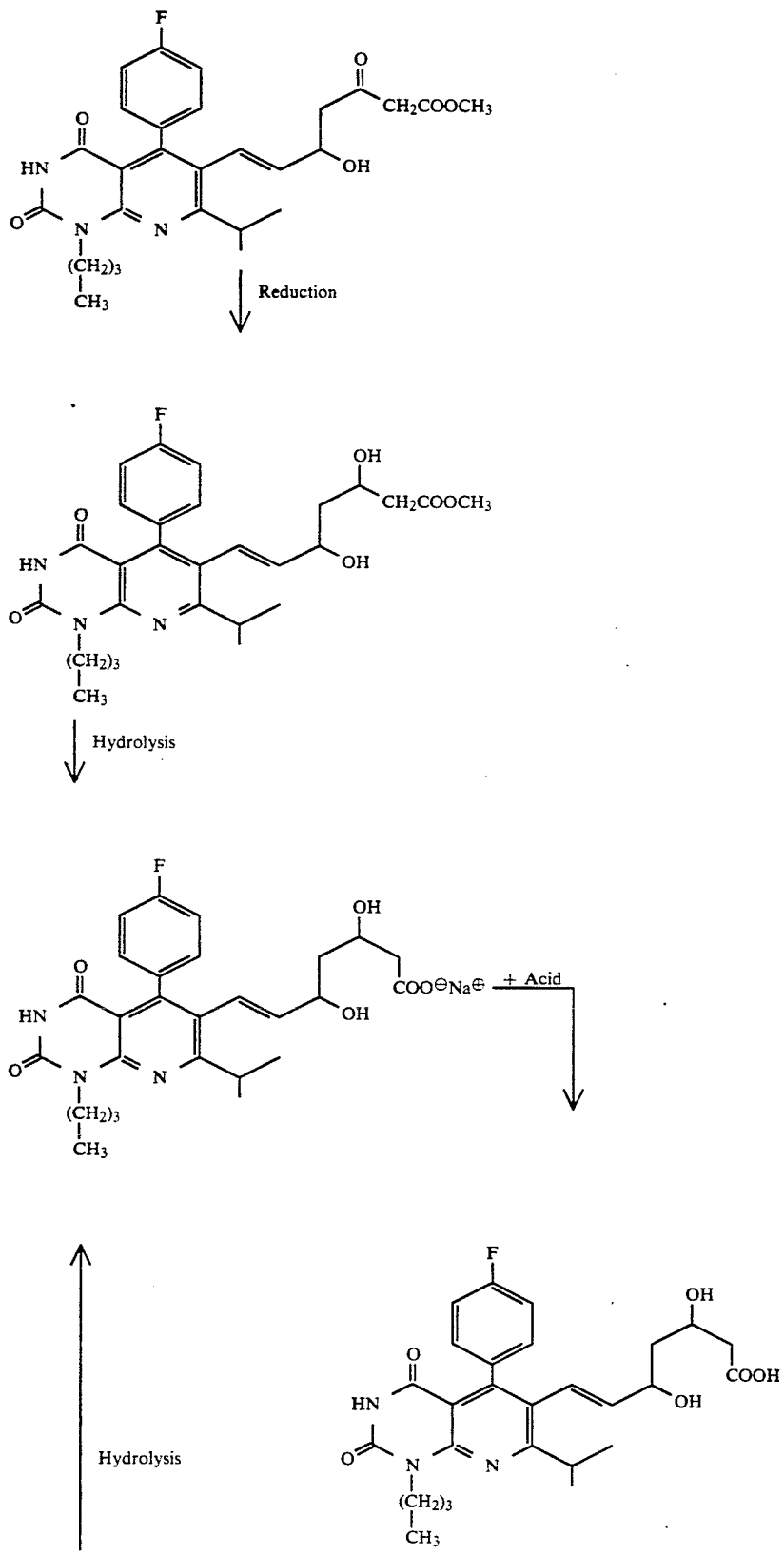

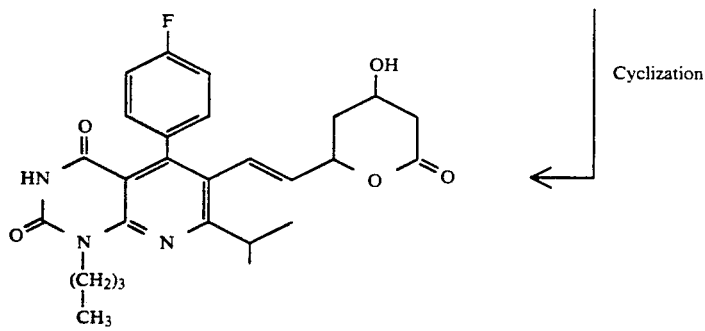

Cyclization

The reduction can be carried out using the customary reducing agents, preferably those which are suitable for the reduction of ketones to hydroxy compounds. Reduction using metal hydrides or complex metal hydrides in inert solvents is particularly suitable in this connection, if appropriate in the presence of a trialkylborane. Preferably, the reduction is carried out using complex metal hydrides such as, for example, lithium borohydride, sodium borohydride, potassium borhydride, zinc borohydride, lithium trialkylborohydrides, sodium trialkylborohydrides, sodium cyanoborohydride or lithium aluminum hydride. Very particularly preferably, the reduction is carried out using sodium borohydride in the presence of triethylborane and methanol.

Suitable solvents in this connection are the customary organic solvents which do not change under the reaction conditions. These preferably include ethers such as, for example, diethyl ether, dioxane, tetrahydrofuran or dimethoxyethane, or halogenated hydrocarbons such as, for example, dichloromethane, trichloromethane, tetrachloromethane, 1,2-dichloroethane, or hydrocarbons such as, for example, benzene, toluene or xylene. It is likewise possible to employ mixtures of the solvents mentioned.

Particularly preferably, the reduction of the ketone group to the hydroxy group is carried out under conditions in which the customary functional groups such as, for example, the alkoxycarbonyl group do not change. The use of sodium borohydride as a reducing agent in the presence of triethylborane and methanol in inert solvents such as, preferably, ethers is particularly preferable for this purpose.

The reduction is in general carried out in a temperature range from −80° C. to +30° C., preferably from −78° C. to 0° C.

The process according to the invention is in general carried out at atmospheric pressure. However, it is also possible to carry out the process at reduced pressure or at elevated pressure (for example in a range from 0.5 to 5 bar).

In general, the reducing agent is employed in an amount from 1 to 2 moles, preferably from 1 to 1.5 moles, relative to 1 mole of the keto compound.

Under the abovementioned reaction conditions, the carbonyl group is in general reduced to the hydroxyl group without reduction of the double bond to a single bond taking place.

In order to prepare compounds of the general formula (I), in which X represents an ethylene grouping, the reduction of the ketones (III) can be carried out under those conditions under which both the carbonyl group and the double bond are reduced.

Moreover, it is also possible to carry out the reduction of the carbonyl group and the reduction of the double bond in two separate steps.

The carboxylic acids in the context of the general formula (I) correspond to the formula (Ic)

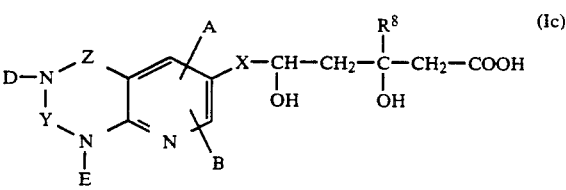

in which
A, B, D, E, X, Y, Z and $R^8$ have the abovementioned meanings,

The carboxylic acid esters in the context of the general formula (I) correspond to the formula (Id)

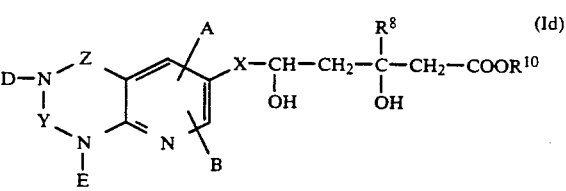

in which
A, B, D, E, X, Y, Z and $R^8$ have the abovementioned meanings, and
$R^{10}$ - represents alkyl having up to 6 carbon atoms.

The salts of the compounds in the context of the general formula (I) according to the invention correspond to the formula (Ie)

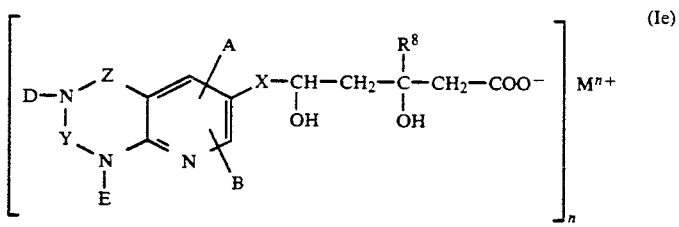

in which

A, B, D, E, X, Y, Z and $R^8$ have the abovementioned meanings, and $M^{n+}$ represents a cation, where n indicates the valency.

The lactones in the context of the general formula (I) correspond to the formula (If)

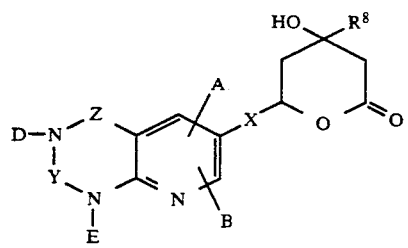

in which

A, B, D, E, X, Y, Z and $R^8$ have the abovementioned meanings,

In order to prepare the carboxylic acids of the general formula (Ic) according to the invention, the carboxylic acid esters of the general formula (Id) or the lactones of the general formula (If) are in general hydrolyzed according to customary methods. Hydrolysis is in general carried out by treating the esters or the lactones in inert solvents with customary bases, the salts of the general formula (Ie) initially resulting, which can subsequently be converted in a second step by treating with acid into the free acids of the general formula (Ic).

Suitable bases for hydrolysis are the customary inorganic bases. These preferably include alkali metal hydroxides or alkaline earth metal hydroxides such as, for example, sodium hydroxide, potassium hydroxide or barium hydroxide, or alkali metal carbonates such as sodium carbonate or potassium carbonate or sodium hydrogen carbonate, or alkali metal alkoxides such as sodium ethoxide, sodium methoxide, potassium methoxide, potassium ethoxide or potassium tert. butoxide. Sodium hydroxide or potassium are particularly preferably employed.

Suitable solvents for hydrolysis are water or the organic solvents customary for hydrolysis. These preferably include alcohols such as methanol, ethanol, propanol, isopropanol or butanol, or ethers such as tetrahydrofuran or dioxane, or dimethylformamide or dimethyl sulphoxide. It is also possible to employ mixtures of the solvents mentioned. Particularly preferably, alcohols such as methanol, ethanol, propanol or isopropanol or a mixture of tetrahydrofuran and water are used.

The hydrolysis is in general carried out in a temperature range from 0° C. to +100° C., preferably from +20° C. to +80° C.

In general, the hydrolysis is carried out at atmospheric pressure. However, it is also possible to work at reduced pressure or elevated pressure (for example from 0.5 to 5 bar).

When carrying out the hydrolysis, the base is in general employed in an amount from 1 to 3 moles, preferably from 1 to 1.5 moles, relative to 1 mole of the ester or the lactone. Equimolar amounts of the reactants are particularly preferably used.

When carrying out the reaction, the salts of the compounds (Ie) according to the invention are formed in the first step as intermediates which can be isolated. The acids (Ic) according to the invention are obtained by treating the salts (Ie) with customary inorganic acids. These preferably include mineral acids such as, for example, hydrochloric acid, hydrobromic acid, sulphuric acid or phosphoric acid. It has proved advantageous in this connection in the preparation of the carboxylic acids (Ic) to acidify the basic reaction mixture from the hydrolysis in a second step without isolation of the salts. The acids can then be isolated in a customary manner.

In order to prepare the lactones of the formula (If) according to the invention, the carboxylic acids (Ic) according to the invention are in general cyclized according to the customary methods, for example by heating the corresponding acid in inert organic solvents, if appropriate in the presence of molecular sieve.

Suitable solvents in this connection are hydrocarbons such as benzene, toluene, xylene, mineral oil fractions, or tetralin or diglyme or triglyme. Benzene, toluene or xylene are preferably employed. It is also possible to employ mixtures of the solvents mentioned. Hydrocarbons, in particular toluene, in the presence of molecular sieve are particularly preferably used.

Cyclization is in general carried out in a temperature range from −40° C. to +200° C., preferably from −25° C. to +110° C.

Cyclization is in general carried out at atmospheric pressure, but it is also possible to carry out the process at reduced pressure or at elevated pressure (for example in a range from 0.5 to 5 bar).

Moreover, the cyclization is also carried out in inert organic solvents, with the aid of cyclizing or dehydrating agents. Carbodiimides are preferably used as dehydrating agents in this connection. N,N'-dicyclohexylcarbodiimide paratoluenesulphonate, N-cyclohexyl-N'-[2-(N''-methylmorpholinium)ethyl]carbodiimide or N-(3-dimethylaminopropyl)-N'-ethylcarbodiimide hydrochloride are preferably employed as carbodiimides.

Suitable solvents in this connection are the customary organic solvents. These preferably include ethers such as diethyl ether, tetrahydrofuran or dioxane, or chlorinated hydrocarbons such as methylene chloride, chloroform or carbon tetrachloride, or hydrocarbons such as benzene, toluene, xylene or mineral oil fractions. Chlorinated hydrocarbons such as, for example, methylene chloride, chloroform or carbon tetrachloride, or hydrocarbons such as benzene, toluene, xylene or mineral oil fractions are particularly preferred. Chlorinated hydrocarbons such as, for example, methylene chloride, chloroform or carbon tetrachloride are particularly preferably employed.

The reaction is in general carried out in a temperature range from 0° C. to +80° C., preferably from +10° C. to +50° C.

When carrying out the cyclization, it has proved advantageous to employ the cyclization method with the aid of carbodiimides as dehydrating agents.

The resolution of the isomers into the stereoisomerically uniform constituents is in general carried out by customary methods such as are described, for example, by E. L. Eliel, Stereochemistry of Carbon Compounds, McGraw Hill, 1962. Resolution of the isomers in the racemic ester step is preferred in this connection. The racemic mixtures of the trans-lactones (VII) is particularly preferably converted in this case by treating either with D-(+)- or L-(−)-α-methylbenzylamine by customary methods into the diastereomeric dihydroxyamides (Ig)

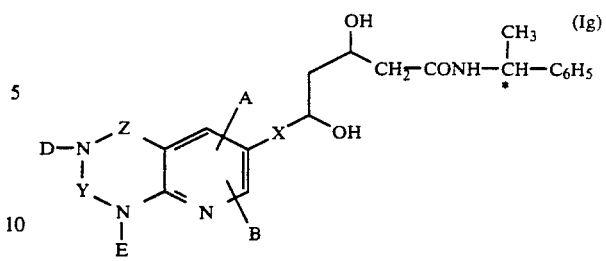

which can then be resolved into the individual diastereomers as is customary by chromatography or crystallization. Subsequent hydrolysis of the pure diastereomeric amides by customary methods, for example by treating the diastereomeric amides with inorganic bases such as sodium hydroxide or potassium hydroxide in water and/or organic solvents such as alcohols, for example methanol, ethanol, propanol or isopropanol, gives the corresponding enantiomerically pure dihydroxy acids (Ic) which can be converted into the enantiomerically pure lactones by cyclization as described above. In general, it is true for the preparation of the compounds of the general formula (I) according to the invention in enantiomerically pure form that the configuration of the final products according to the methods described above is dependent on the configuration of the starting substances.

The resolution of isomers is intended to be illustrated by way of example in the following scheme:

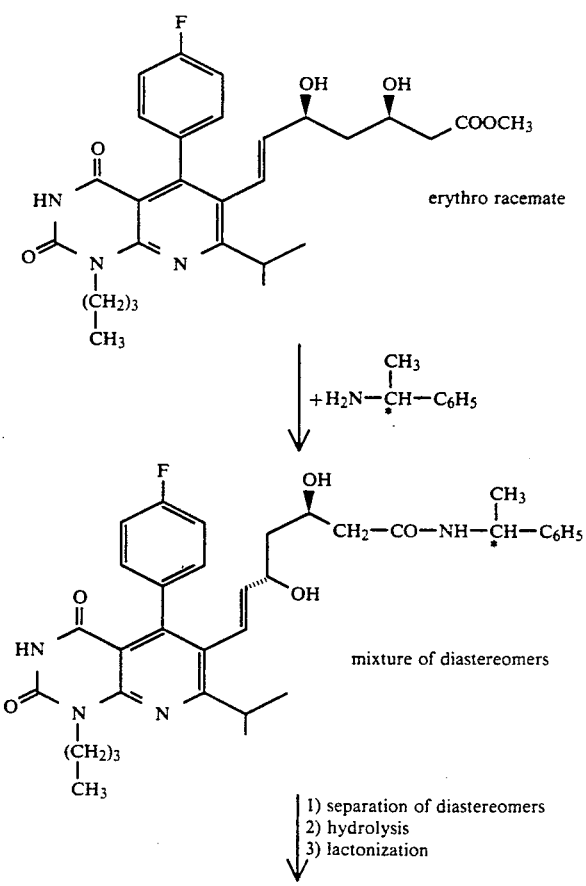

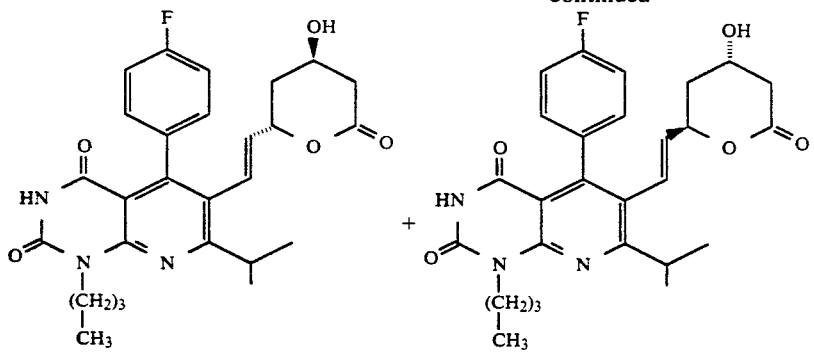

The ketones (VIII) employed as starting substances are new.

A process for the preparation of the ketones of the general formula (VIII) according to the invention

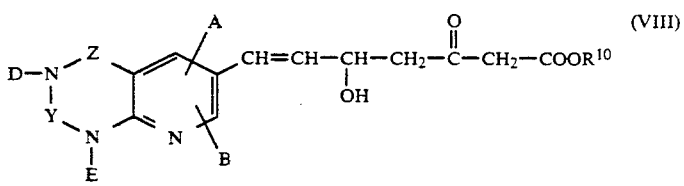

in which

A, B, D, E, Y, Z and $R^{10}$ have the abovementioned meanings, has been found which is characterized in that aldehydes of the general formula (IX)

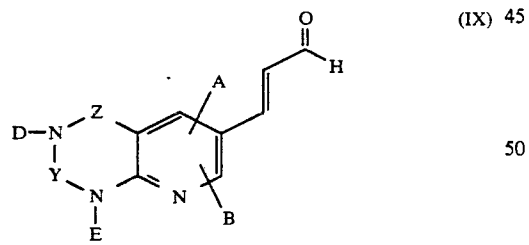

in which

A, B, D, E, Y and Z have the abovementioned meanings, are reacted in inert solvents with acetoacetic esters of the general formula (X)

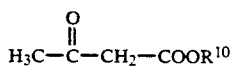

in which $R^{10}$ has the abovementioned meaning, in the presence of bases.

The process according to the invention can be illustrated, for example, by the following equation:

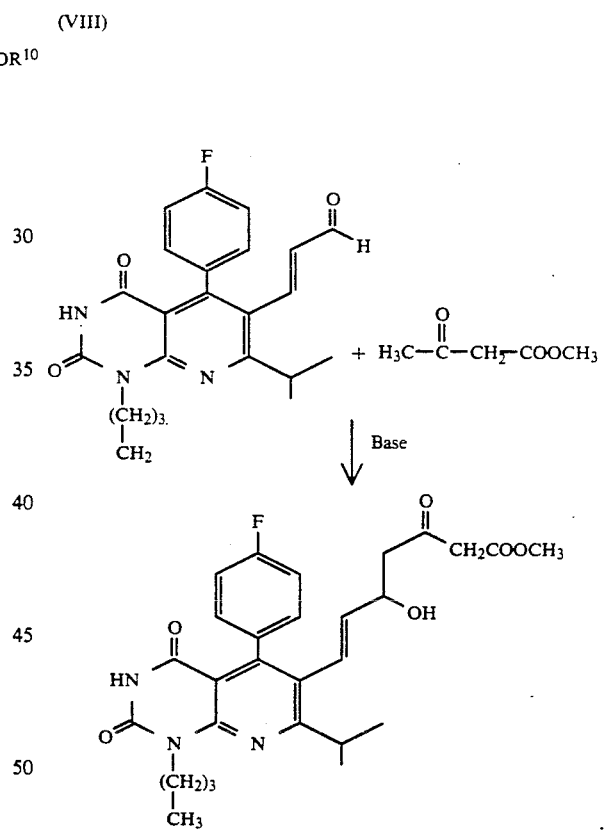

Suitable bases in this connection are the customary strong basic compounds. These preferably include organolithium compounds such as, for example, N-butyllithium, sec. butyllithium, tert. butyllithium or phenyllithium, or amides such as, for example, lithium diisopropylamide, sodium amide or potassium amide, or lithium hexamethyldisilylamide, or alkali metal hydrides such as sodium hydride or potassium hydride. It is likewise possible to employ mixtures of the bases mentioned. N-butyllithium or sodium hydride or a mixture thereof is particularly preferably employed.

Additions of metal halides such as, for example, magnesium chloride, zinc chloride or zinc bromide may be advantageous. The addition of zinc halides is particularly preferred.

Suitable solvents in this connection are the customary organic solvents which do not change under the reaction conditions. These preferably include ethers such as diethyl ether, tetrahydrofuran, dioxane or dimethoxyethane, or hydrocarbons such as benzene, toluene, xylene, cyclohexane, hexane or mineral oil fractions. It is likewise possible to employ mixtures of the solvents mentioned. Ethers such as diethyl ether or tetrahydrofuran are particularly preferably used.

The reaction is in general carried out in a temperature range from −80° C. to +50° C., preferably from −20° C. to room temperature.

The process is in general carried out at atmospheric pressure, but it is also possible to carry out the process at reduced pressure or elevated pressure, for example in a range from 0.5 to 5 bar.

When carrying out the process, the acetoacetic ester is in general employed in an amount from 1 to 3, preferably from 1 to 2, moles, relative to 1 mole of the aldehyde.

The acetoacetic esters of the formula (X) employed as starting substances are known or can be prepared by known methods [Beilstein's Handbuch der organischen Chemie (Beilstein's Handbook of Organic Chemistry) III, 62; 438].

Examples of acetoacetic esters for the process according to the invention which may be mentioned are: methyl acetoacetate, ethyl acetoacetate, propyl acetoacetate and isopropyl acetoacetate.

The preparation of the aldehydes of the general formula (IX) employed as starting substances is intended to be illustrated below by way of example for the 1,2,3,4-tetrahydro-pyrido(2,3-d)pyrimidines of the type (Ia).

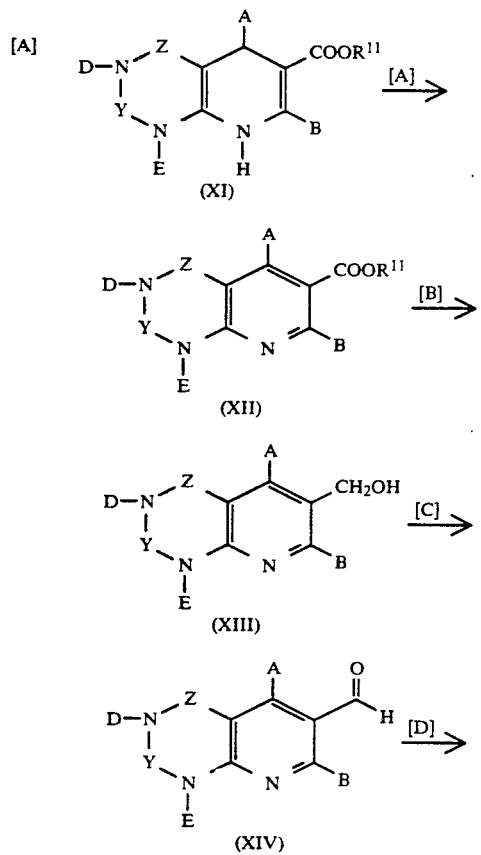

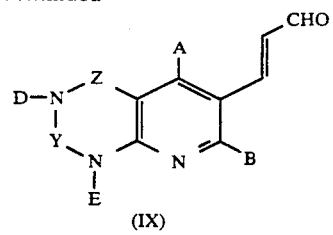

In this connection, the 1,2,3,4,5,8-hexahydropyrido(2,3-d)pyrimidines of the general formula (XI), in which $R^{11}$ stands for an alkyl radical having up to 4 carbon atoms, are oxidized in suitable solvents using suitable oxidizing agents as in the first step [A]. Preferably 1,2,3,4-hexahydro-pyrido(2,3-d)pyrimidines in chlorinated hydrocarbons such as, for example, methylene chloride, are oxidized with 2,3-dichloro-4,5-dicyano-p-benzoquinone at room temperature, or with chromium trioxide in glacial acetic acid at elevated temperatures, preferably at reflux temperature, to give the 1,2,3,4-tetrahydro-pyrido(2,3-d)pyrimidines (XII).

In the second step [B], the 1,2,3,4-tetrahydropyrido(2,3-d)pyrimidines (XII) are reduced in inert solvents such as ethers, for example diethyl ether, tetrahydrofuran or dioxane, or in hydrocarbons, for example benzene or toluene, preferably in tetrahydrofuran or toluene, using metal hydrides as reducing agents, for example lithium aluminum hydride, sodium cyanoborohydride, sodium aluminum hydride, diisobutylaluminum hydride or sodium bis-(2-methoxyethoxy)-dihydroaluminate, in temperature ranges from −70° C. to +100° C., preferably from −70° C. to room temperature, or from room temperature to 70° C. depending on the reducing agent used to give the hydroxymethyl compounds (XIII). The reduction is preferably carried out using diisobutylaluminum hydride in tetrahydrofuran in a temperature range from −78° C. to room temperature. In the third step [C], the hydroxymethyl compounds (XIII) are oxidized by customary methods to give the aldehydes (XIV). The oxidation can be carried out, for example, with pyridinium chlorochromate, if appropriate in the presence of alumina, in inert solvents such as chlorinated hydrocarbons or ethers, preferably methylene chloride or tetrahydrofuran, at room temperature or with trifluoroacetic anhydride and dimethyl sulphoxide (Swern oxidation) or else by other methods customary for the oxidation of hydroxymethyl compounds to aldehydes. In the fourth step [D], the aldehydes (XIV) are converted into the compounds (IX) by reacting with diethyl 2-(cyclohexylamino)-vinyl-phosphonate or with 1,3-dioxane-2-yl-methyl-triphenylphosphonium bromide in inert solvents such as ethers or dimethylformamide, preferably in tetrahydrofuran in the presence of sodium hydride or sodium ethoxide, in a temperature range from −20° C. to +30° C., preferably from −5° C. to room temperature.

The compounds of the general formula (IX), in which D has the abovementioned meaning, but does not represent hydrogen, can be prepared by alkylating compounds of the general formula (IXa)

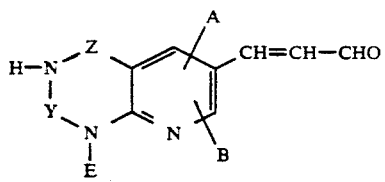

(IXa)

in which

A, B, E, Y and Z have the abovementioned meanings, to introduce D, using alkyl halides, preferably alkyl iodide, for example methyl iodide, in the presence of the abovementioned bases, preferably sodium hydride or using activated olefins, such as, for example, acrylonitrile in the abovementioned inert solvents, preferably tetrahydrofuran.

The compounds of the general formula (XI) employed as starting substances are known per se or can be prepared by customary methods [compare German Offenlegungsschrift DE 2,738,153, U.S. Pat. No. 4,596,805; V. Papesch, E. F. Schroeder, J. Org. Chem. 13, 1879, (1951); T. Kishihawe, H. Yuhi, Chem. Pharm. volume 14, 1365-1370 (1966)].

The starting compounds of the general formulae (XII), (XIII) and (XIV) are known per se or can be prepared by customary methods [Chem. Ber. 101 (2), 512-521; J. Heterocycl. Chem., 22 (2), 345-347; Khim. Geterosikl. Soedin., (6), 834-837; Farmaco, Ed. Sci. 37 (4), 247-258].

The compounds of the general formula (I) according to the invention possess useful pharmacological properties and can be employed in medicaments. In particular, they are inhibitors of 3-hydroxy-3-methyl-glutaryl-coenzyme A (HMG-CoA) reductase and, as a result of this, inhibitors of cholesterol biosynthesis. They can therefore be employed for the treatment of hyperlipoproteinaemia, lipoproteinaemia or atherosclerosis. The active substances according to the invention additionally cause a lowering of the cholesterol content in the blood.

The enzyme activity determination was carried out as modified by G. C. Ness et al., Archives of Biochemistry and Biphysics 197, 493-499 [1979]. Male Rico rats (body weight 300-400 g) were treated for 11 days with altromin powdered feed to which 40 g of cholestyramine/kg of feed had been added. After description, the livers were removed from the animals and placed on ice. The livers were comminuted and homogenized 3 times in 3 volumes of 0.1 m sucrose, 0.05 m KCl, 0.04 m $K_xH_y$ phosphate, 0.03 m ethylenediaminetetraacetic acid, 0.002 m dithiothreitol [SPE] buffer pH 7.2 in a Potter-Elvejem homogenizer. The mixture was then centrifuged at 15,000 g for 15 minutes and the sediment was discarded. The supernatant was sedimented at 100,000 g for 75 minutes. The pellet was taken up in ¼ volumes of SPE buffer, homogenized once more and then centrifuged again at 100,000 g for 60 minutes. The pellet was taken up using a 5-fold amount of its volume of SPE buffer, homogenized and frozen and stored at −78° C. (=enzyme solution).

For testing, the test compounds (or mevinolin as a reference substance) were dissolved in diemthylformamide with the addition of 5 vol.-% of 1 N NaOH and, using 10 μl, employed in the enzyme test in various concentrations. The test was started after preincubation of the compounds with the enzyme at 37° C. for 20 minutes. The test batch was 0.380 ml and contained 4 μmol of glucose-6-phosphate, 1.1 mg of bovine serum albumin, 2.1 μmol of dithiothreitol, 0.35 μmol of NADP, 1 unit of glucose-6-phosphate dehydrogenase, 35 μmol of $K_xH_y$ phosphate pH 7.2, 20 μl of enzyme preparation and 56 nmol of 3-hydroxy-3-methyl-glutaryl-coenzyme A (glutaryl-3-$^{14}$C) 100,000 dpm.

After incubating for 60 minutes at 37° C., the batch was centrifuged and 600 μl of the supernatant was applied to a 0.7×4 cm column packed with a 5-chloride 100-200 mesh (anion exchanger). The column was subsequently washed with 2 ml of distilled water and 3 ml of Aquasol were added to runnings plus washing water and counted in an LKB scintillation counter. IC$_{50}$ values were determined by intrapolation by plotting the percentage inhibition against the concentration of the compound in the test. In order to determine the relative inhibitory potency, the IC$_{50}$ value of the reference substance mevinolin was set at 1 and compared with the simultaneously determined IC$_{50}$ value of the test compound.

| Relative in vitro activities | |
|---|---|
| Example No. | relative activity (mevinolin = 1) |
| 8 | 2 |
| 16 | 6 |

The new active substances can be converted in a known manner into the customary formulations, such as tablets, coated tablets, pills, granules, aerosols, syrups, emulsions, suspensions and solutions, using insert, nontoxic, pharmaceutically suitable excipients or solvents. In this connection, the therapeutically active compound should in each case be present in a concentration of about 0.5 to 98% by weight, preferably 1 to 90% by weight, of the total mixture, i.e. in amounts which are sufficient in order to achieve the dosage range indicated.

The formulations are prepared, for example, by extending the active compounds with solvents, and/or excipients, if appropriate using emulsifiers and/or dispersants, where, for example, in the case of the use of water as a diluent, if appropriate organic solvents can also be used as auxiliary solvents.

Examples of auxiliaries which may be mentioned are: water, non-toxic organic solvents, such as paraffins (for example mineral oil fractions), vegetable oils (for example groundnut/sesame oil), alcohols (for example: ethyl alcohol, glycerol), excipients, such as, for example, ground natural minerals (for example, kaolins, clays, talc, chalk), ground synthetic minerals (for example highly disperse silica, silicates), sugars (for example sucrose, lactose and dextrose), emulsifiers (for example polyoxyethylene fatty acid esters, polyoxyethylene fatty alcohol ethers, alkyl sulphonates and aryl sulphonates), dispersing agents (for example ligninsulphate waste liquors, methylcellulose, starch and polyvinylpyrrolidone) and lubricants (for example magnesium stearate, talc, stearic acid and sodium lauryl sulphate).

Administration is carried out in a customary manner, preferably orally, parenterally, perlingually or intravenously. In the case of oral administration, tablets may of course also contain additions, such as sodium citrate, calcium carbonate and dicalcium phosphate together with various additives, such as starch, preferably potato starch, gelatin and the like in addition to the excipients mentioned. Furthermore, lubricants, such as magnesium stearate, sodium lauryl sulphate and talc can additionally be used for tableting. In the case of aqueous suspensions, various flavor enhancers or colorants may be added to the active compounds in addition to the above-mentioned auxiliaries.

In the case of paraneteral administration, solutions of the active compounds using suitable liquid excipients may be employed.

In general, it has proved advantageous on intravenous administration to administer amounts of about 0.001 to 1 mg/kg, preferably about 0.01 to 0.5 mg/kg of body weight to attain effective results, and on oral administration the dosage is about 0.01 to 20 mg/kg, preferably 0.1 to 10 mg/kg of body weight.

In spite of this it may be necessary to deviate from the amounts mentioned, depending on the body weights or the type of administration route, on individual behaviour towards the medicament, the manner of its formulation and the point in time or interval at which administration takes place.

Thus in some cases it may be sufficient to manage with less than the minimum amount previously mentioned, whereas in other cases the upper limit mentioned must be exceeded. In the case of the administration of larger amounts, it may be advisable to divide these into a number of individual doses over the day.

Preparation examples

EXAMPLE 1

E,Z-2-Ethoxycarbonyl-1-(4-fluorophenyl)-4-methyl-pent-1-en-3-one

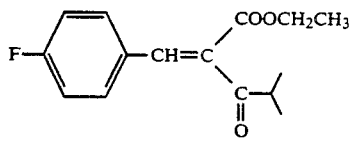

A solution of 20 ml (0.2 mol) of piperidine and 12 ml (0.21 mmol) of acetic acid in 200 ml of isopropanol is added to 554 g (3.5 mol) of ethyl isobutyryl acetate and 434 g (3.5 mol) of 4-fluorobenzaldehyde in 1.8 l of isopropanol. The mixture is stirred at room temperature for 1 day and concentrated in vacuo, and the residue is distilled in a high vacuum.

Yield: 796 g (86% of theory) of yellowish oil.
b.p.: 135°-140° C. (0.2 mbar).

EXAMPLE 2

1-Butyl-6-ethoxycarbonyl-5-(4-fluorophenyl)-7-isopropyl-2,4-dioxo-1,2,3,4,5,8-hexahydro-pyrido(2,3-d)pyrimidine

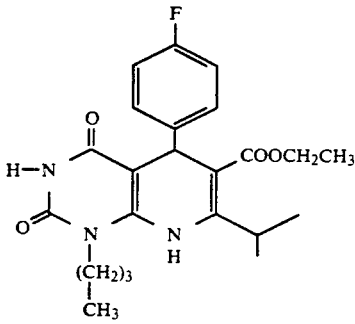

91.6 g (0.5 mol) of 6-amino-1-butyl-uracil and 145.4 g (0.55 mol) of the compound from Example 1 are heated at reflux overnight in 750 ml of isopropanol. A further 39.6 g (0.15 mol) of the compound from Example 1 are added and the mixture is boiled for a further day. The precipitate which deposits is filtered off with suction and subsequently washed with a little isopropanol.

Yield: 143.9 g (67% of theory) of colorless crystals.
m.p.: 214° C. (from methanol).

EXAMPLE 3

1-Butyl-6-ethoxycarbonyl-5-(4-fluorophenyl)-7-isopropyl-2,4-dioxo-1,2,3,4-tetrahydro-pyrido(2,3-d)pyrimidine

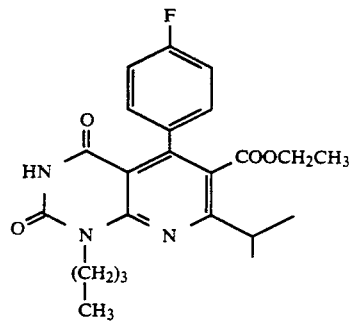

11.35 g (50 mmol) of 2,3-dichloro-4,5-dicyanobenzoquinone are added to a mixture of 21.5 g (50 mmol) of the compound from Example 2 in 800 ml of dichloromethane and the mixture is stirred at room temperature for 1 h. The solution is filtered from a beige precipitate, the filtrate is washed four times with water, the organic phase is dried over sodium sulphate, filtered through a thin layer of active carbon and the filtrate is concentrated in vacuo. The residue is crystallized from ether/petroleum ether.

Yield: 20.1 g (94% of theory) of colorless crystals.
m.p.: 129° C.

EXAMPLE 4

1-Butyl-5-(4-fluorophenyl)-6-hydroxymethyl-7-isopropyl-2,4-dioxo-1,2,3,4-tetrahydro-pyrido(2,3-d)pyrimidine

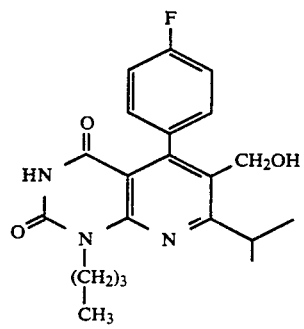

135 ml of a 1 molar solution of diisobutylaluminum hydride in toluene are slowly added under argon to a suspension of 19.2 g (45 mmol) of the compound from Example 3 in 400 ml of toluene at −75° C., which leads to a clear solution. After 1 hour, a further 30 ml of dibutylaluminum hydride solution are added at the same temperature, the mixture is stirred for a further hour and then allowed to warm to room temperature, 400 ml of water and 200 ml of ethyl acetate being added cautiously from −30° C. The mixture is filtered off with suction through kieselguhr and subsequently washed with ethyl acetate. After phase separation, the aqueous phase is extracted with ethyl acetate, and the combined organic phases are washed with sodium chloride solution, dried over sodium sulphate and concentrated in vacuo. The residue is chromatographed in a column (φ 6 cm) on 500 g of 230–400 mesh silica gel using petroleum ether/ethyl acetate (2:1).

Yield: 11.8 g (68% of theory) of colorless crystals.
m.p.: 99° C. (from ether/petroleum ether).

EXAMPLE 5

1-Butyl-5-(4-fluorophenyl)-6-formyl-7-isopropyl-2,4-dioxo-1,2,3,4-tetrahydro-pyrido(2,3-d)pyrimidine

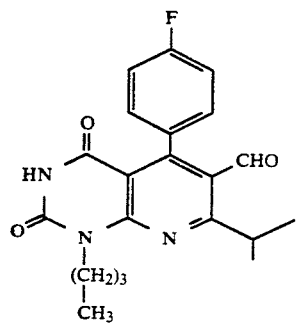

8.5 g (22 mmol) of the compound from Example 4 are dissolved in 220 ml of dichloromethane, 4.5 g of neutral alumina and 9.5 g (44 mmol) of pyridinium chlorochromate are added and the mixture is stirred at room temperature for 1 h. The mixture is filtered through a silica gel bed, without sucking dry, and subsequently washed with dichloromethane, and the filtrate is concentrated to dryness in vacuo. The residue is chromatographed on 150 g of 230–400 mesh silica gel in a column (φ 4 cm) using petroleum ether/ethyl acetate 2:1.

Yield: 7.6 g (90% of theory) of colorless solid.
m.p.: 179° C.

EXAMPLE 6

(E)-3-[1-Butyl-5-(4-fluorophenyl)-7-isopropyl-2,4-dioxo-1,2,3,4-tetrahydro-pyrido(2,3-d)pyrimidin-6-yl]prop-2-enal

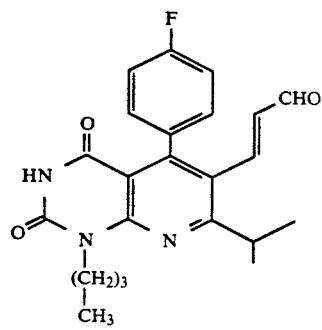

A solution of 1.15 g (4.4 mol) of diethyl 2-(cyclohexylamino)-vinyl-phosphonate in 15 ml of tetrahydrofuran is added dropwise in the course of 10 min at 0°–5° C. under argon to a suspension of 0.25 g (8.4 mmol) of 80% strength sodium hydride in 15 ml of anhydrous tetrahydrofuran. The mixture is stirred at 0° C. for 15 min, a solution of 1.5 g (4 mmol) of the compound from Example 5 in 15 ml of tetrahydrofuran is added dropwise at 0° C. in the course of 20 min, and the mixture is stirred at room temperature for 1 h and under reflux for 20 min. The mixture is cooled, 50 ml of water are added cautiously, the mixture is extracted twice with ethyl acetate, and the combined organic phases are washed with sodium chloride solution and concentrated in vacuo. The residue is heated under reflux with a mixture of 25 ml of toluene, 35 ml of water and 2.6 g (36 mmol) of oxalic acid dihydrate for 1 h. The phases are separated, the aqueous phase is extracted with ethyl acetate, and the combined organic phases are washed with sodium chloride solution, dried over magnesium sulphate and concentrated in vacuo. The residue is crystallized from ether/petroleum ether.

Yield: 1.0 g (61% of theory) of yellowish solid.
m.p.: 162° C.

EXAMPLE 7

Methyl (E)-7-[1-butyl-5-(4-fluorophenyl)-7-isopropyl-2,4-dioxo-1,2,3,4-tetrahydro-pyrido(2,3-d)pyrimidin-6-yl]-5-hydroxy-3-oxo-hept-6-enoate

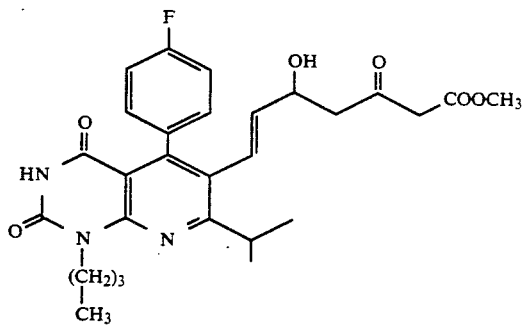

0.7 g (6 mmol) of methyl acetoacetate are added dropwise at 0°–5° C. to a suspension of 0.2 g (6.6 mmol) of 80% strength sodium hydride in 8 ml of anhydrous tetrahydrofuran. After 15 min, 4.9 ml (8 mmol) of 15% strength butyllithium in hexane are added dropwise in the course of 10 min and the mixture is kept at 0° C. for a further 15 min. 0.82 g (2 mmol) of the compound from Example 6 and 10 ml of tetrahydrofuran are then added and the mixture is stirred at 0°–5° C. for 1 h. 1.2 g (20 mmol) of acetic acid in 20 ml of water are then added cautiously, the mixture is extracted three times with ethyl acetate, and the organic phase is washed with sodium chloride solution, dried over sodium sulphate and concentrated in vacuo. The residue is chromatographed on 40 g of 230–400 mesh silica gel (φ 3 cm) using petroleum/ethyl acetate (2:1) to (1:3).

Yield: 0.14 g (13% of theory) of yellow oil.
$R_f$=0.3 (petroleum ether/ethyl acetate 1:1).

EXAMPLE 8

Methyl erythro-(E)-7-[1-butyl-5-(4-fluorophenyl)-7-isopropyl-2,4-dioxo-1,2,3,4-terahydro-pyrido(2,3-d)pyrimidin-6-yl]-3,5-dihydroxy-hept-6-enoate

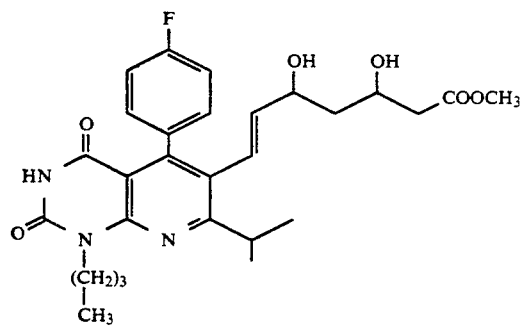

0.29 ml of a 1 molar solution of triethylborane in tetrahydrofuran is added to a solution of 126 mg (0.24 mmol) of the compound from Example 7 in 4 ml of anhydrous terahydrofuran and air is blown through the solution for 5 min. 11.4 mg (0.3 mmol) of sodium borohydride are added at $-78°$ C., then 0.5 ml of methanol is added dropwise and the mixture is kept at $-78°$ C. to $-75°$ C. for 1 h. It is then allowed to warm to room temperature, 1 ml of 30% strength hydrogen peroxide and 20 ml of water being added at $-30°$ C. The mixture is extracted four times with ethyl acetate, and the combined organic phases are washed with sodium chloride solution, dried over sodium sulphate and concentrated. The residue is chromatographed on 15 g of silica gel (230–400 mesh) in a column ($\phi$ 2 cm) using petroleum ether/ethyl acetate (1:1).

Yield: 52 mg (41% theory) of colorless solid.
m.p.: 171° C.

EXAMPLE 9

Erythro-(E)-7-[1-butyl-5-(4-fluorophenyl)-7-isopropyl-2,4-dioxo-1,2,3,4-tetrahydro-pyrido(2,3-d)pyrimidin-6-yl]-3,5-dihydroxy-hept-6-ene carboxylic acid sodium salt

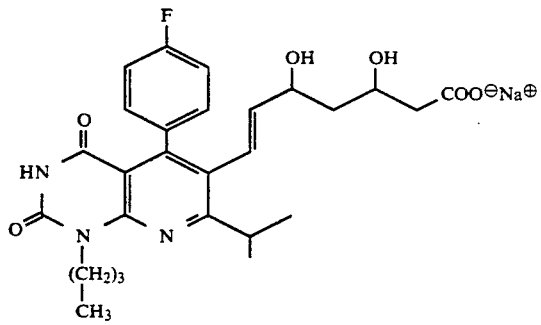

A solution of 27 mg (0.05 mmol) of the compound from Example 8 in 1 ml of tetrahydrofuran is stirred with 0.5 ml (0.05 mmol) of a 0.1 molar sodium hydroxide solution at room temperature for 2 h. The mixture is concentrated and dried over phosphorus pentoxide in vacuo.

Yield: 22 mg (82% of theory) of colorless solid.
FAB-MS: 536 (M+H), 558 (M+Na).

EXAMPLE 10

6-Ethoxycarbonyl-5-(4-fluorophenyl)-7-isopropyl-1-methyl-2,4-dioxo-1,2,3,4,5,8-hexahydro-pyrido(2,3-d)pyrimidine

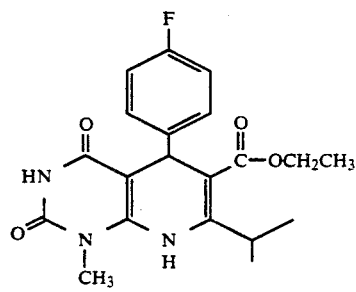

39.5 g (0.28 mol) of 6-amino-1-methyl-uracil and 147.8 g (0.56 mol) of the compound from Example 1 are heated to 180° C. for 4 h. A further 73.9 g (0.28 mol) of the compound from Example 1 are then added and the mixture is heated again for 4 h. After cooling, the mixture is stirred thoroughly with 400 ml of methanol and the precipitate is filtered off with suction.

Yield: 78.2 g (72% of theory) of yellowish solid.
m.p.: 277° C.

EXAMPLE 11

6-Ethoxycarbonyl-5-(4-fluorophenyl)-7-isopropyl-1-methyl-2,4-dioxo-1,2,3,4-tetrahydro-pyrido(2,3-d)pyrimidine

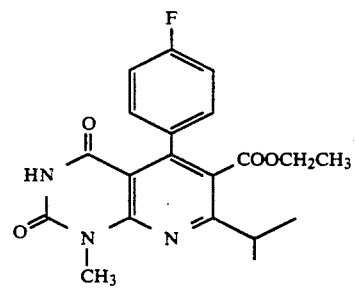

11.35 g (50 mmol) of 2,3-dichloro-4,5-dicyanobenzoquinone are added to a suspension of 19.4 g (50 mmol) of the compound from Example 10 in 1 l of dichloromethane and the mixture is stirred at room temperature for 2 h. It is then washed three times with water, and the organic phase is treated with sodium sulphate and active carbon, filtered and concentrated to dryness. 17.5 g (91% of theory) of colorless solid remain.

m.p.: 214° C.

EXAMPLE 12 AND EXAMPLE 13

5-(4-Fluorophenyl)-6-hydroxymethyl-7-isopropyl-1-methyl-2,4-dioxo-1,2,3,4-tetrahydro-pyrido(2,3-d)pyrimidine

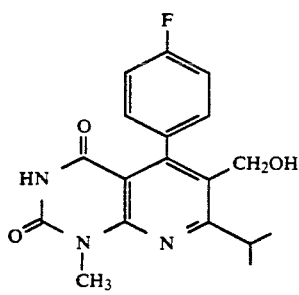
(12)

5-(4-Fluorophenyl)-6-hydroxymethyl-7-isopropyl-1-methyl-4-oxo-1,2,3,4-tetrahydro-pyrido(2,3-d)pyrimidine

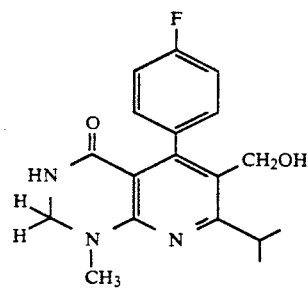
(13)

A product mixture of the abovementioned compounds 12 and 13, which is separated in a column (φ 6 cm) on 400 g of 230-400 mesh silica gel using a gradient of petroleum ether/ethyl acetate (2:1) to (1:3), is obtained from 13.5 g (35 mmol) of the compound from Example 11 and 85.5 ml (128 mmol) of a 1.5 M solution of diisobutyl aluminum hydride in toluene analagously to the process of Example 4.

| $R_f$ | (petroleum ether/ethyl acetate, 1:1) |
|---|---|
| | Ex. 12 = 0.5 |
| | Ex. 13 = 0.2 |
| Yield: | Ex. 12 = 2.4 g (20% of theory) of colorless solid |
| | Ex. 13 = 1.9 g (17% of theory) of colorless solid |
| m.p.: | Ex. 12 = 208° C. |
| | Ex. 13 = 197° C. |

EXAMPLE 14

5-(4-Fluorophenyl)-6-formyl-7-isopropyl-1-methyl-2,4-dioxo-1,2,3,4-tetrahydro-pyrido(2,3-d)pyrimidine

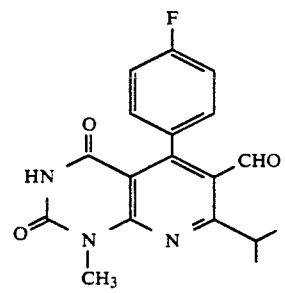

1.4 g (68% of theory) of the title compound are obtained as colorless crystals from 2.1 g (6 mmol) of the compound from Example 12 in 320 ml of dichloromethane using 2.4 g of alumina and 5.2 g (24 mmol) of pyridinium chlorochromate analogously to the process of Example 5.

m.p.: 217° C.

EXAMPLE 15

(E)-3-[5-(4-Fluorophenyl)-7-isopropyl-1-methyl-2,4-dioxo-1,2,3,4-tetrahydro-pyrido(2,3-d)pyrimidin-6-yl)prop-2-enal

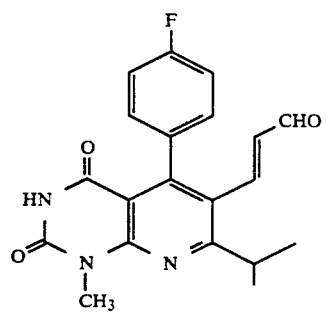

Analogously to the procedure for Example 6, 0.25 g (8.4 mmol) of 80% strength sodium hydride, 1.2 g (4.2 mol) of diethyl 2-(cyclohexylamino)-vinyl-phosphonate and 1.2 g (3.5 mmol) of the compound from Example 14 are reacted in a total of 36 ml of anhydrous tetrahydrofuran, the mixture being heated under reflux for 1 h.

Yield: 1.2 g (93% theory) of yellowish crystals.

m.p.: 202° C.

EXAMPLE 16

Methyl erythro-(E)-7-[5-(4-fluorophenyl)-7-isopropyl-1-methyl-2,4-dioxo-1,2,3,4-tetrahydro-pyrido(2,3-d)pyrimidin-6-yl]-3,5-dihydroxy-hept-6-enoate

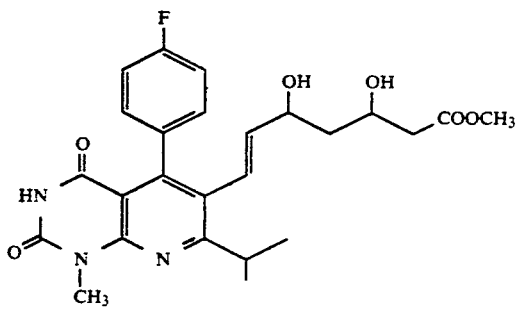

Analogously to the procedures for Example 7 and 8, 140 mg (10% of theory) of the title compound are obtained as colorless crystals from 1.1 g (3 mmol) of the compound from Example 15.

m.p.: 168° C. (from ether/petroleum ether).

EXAMPLE 17

5-(4-Fluorophenyl)-6-formyl-7-isopropyl-1-methyl-4-oxo-1,2,3,4-tetrahydro-pyrido(2,3-d)pyrimidine

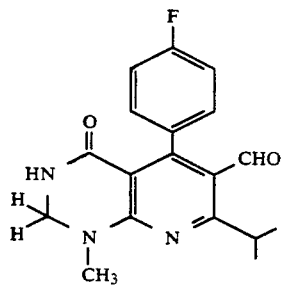

Analogously to the procedure for Example 5, a mixture, which is separated by column chromatography on silica gel using dichloromethane/methanol 40:1, is obtained from 1.72 g (5 mmol) of the compound from Example 13.

Yield: 0.83 g (51% of theory) of colorless crystals.
m.p.: 211° C. from dichloromethane/ether.
$R_f$=0.33 (chloroform/methanol 20:1).

As a by-product, 0.55 g (34% of theory) of 5-(4-fluorophenyl)-6-formyl-7-isopropyl-1-methyl-4-oxo-1,4-dihydro-pyrido(2,3-d)pyrimidine are obtained as a colorless foam.

$R_f$=0.24 (chloroform/methanol 20:1).

$^1$H-NMR (CDCl$_3$): δ=6.95–7.1 (m, 4H); 6.2 (d, 1H); 5.18 (dd, 1H); 4.25 (m, 1H); 4.07 (m, 1H); 3.75 (s, 3H); 3.6 (b, 1H); 3.29 (m, 1H); 3.12 (s, 3H); 2.4 (b, 1H); 2.4 (m, 2H); 1.15–1.45 (m, 2H); 1.15 (m, 6H).

EXAMPLE 18

Methyl erythro-(E)-7-[5-(4-fluorophenyl)-7-isopropyl-1-methyl-4-oxo-1,2,3,4-tetrahydro-pyrido(2,3-d)pyrimidin-6-yl]-3,5-dihydroxy-hept-6-enoate

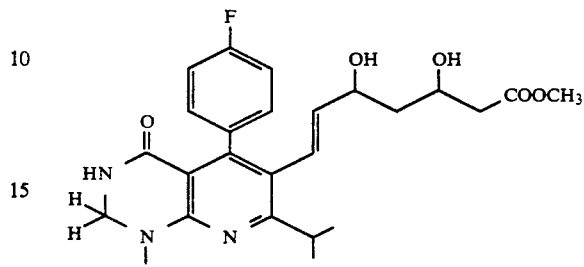

Analogously to the procedures for Example 15, 7 and 8, 115 mg (10% of theory) of colorless crystals are obtained from 0.82 g (2.5 mmol) of the compound from Example 17.

m.p.: 139° C. (dichloromethane/ether).

EXAMPLE 19

E/Z-1-(4-Fluorophenyl)-2-methoxycarbonyl-4-methyl-pent-1-en-3-one

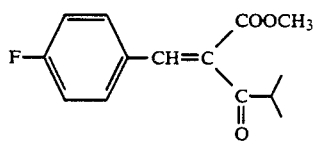

Analogously to the procedure for Example 1, 840.7 g (84% of theory) of the title compound are obtained as a yellowish oil from 496.5 g (4 mol) of 4-fluorobenzaldehyde and 576.7 g (4 mol) of methyl isobutyrylacetate in 1 l of isopropanol using 22.5 ml of piperidine and 13.5 ml of glacial acetic acid.

b.p.: 150°–152° C. (4 mbar).

EXAMPLE 20

(E)-3-[1-Ethyl-5-(4-fluorophenyl)-7-isopropyl-2,4-dioxo-1,2,3,4-tetrahydro-pyrido(2,3-d)pyrimidin-6-yl]prop-2-enal

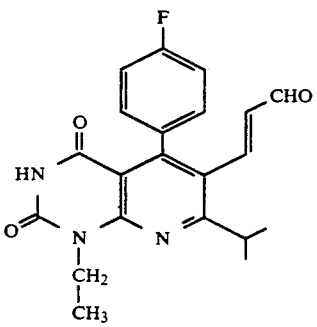

Starting from the compound from Example 19 and 6-amino-1-ethyl-uracil, the compound is obtained as yelllowish crystals analogously to the procedures for Example 10, 11, 4, 14 and 15.

m.p.: 208° C.

EXAMPLE 21

Methyl erythro-(E)-7-[1-ethyl-5-(4-fluorophenyl)-7-isopropyl-2,4-dioxo-1,2,3,4-tetrahydro-pyrido(2,3-d)pyrimidin-6-yl]-3,5-dihydroxy-hept-6-enoate

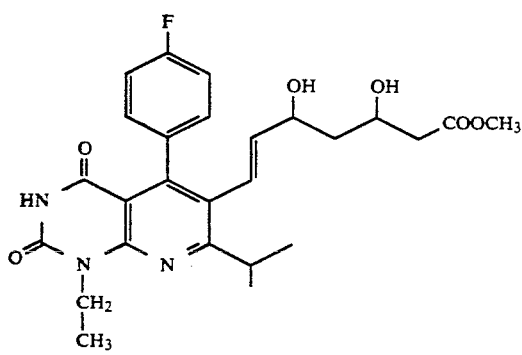

Analogously to the procedures for Example 7 and 8, 0.5 g (33% of theory) of the title compound is obtained as a colorless solid from 1.15 g (3 mmol) of the compound from Example 20.

m.p.: 155° C.

EXAMPLE 22

E-3-[1-Ethyl-5-(4-fluorophenyl)-7-isopropyl-3-methyl-2,4-dioxo-1,2,3,4-tetrahydro-pyrido(2,3-d)pyrimidin-6-yl]-prop-2-enal

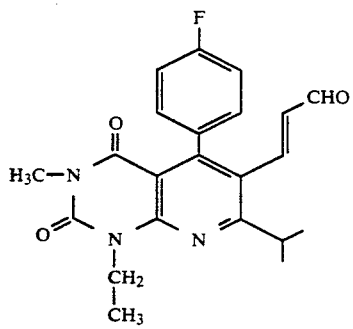

A solution of 1.9 g (5 mmol) of the compound from Example 20 in 15 ml of tetrahydrofuran is added dropwise under argon and with ice cooling to a suspension of 0.18 g (6 mmol) of 80% strength sodium hydride in 10 ml of anhydrous tetrahydofuran. After 20 min, 1.1 ml (18 mmol) of methyl iodide are added and the mixture is stirred overnight at 50° C. 50 ml of water are added cautiously, the mixture is extracted twice with ethyl acetate, and the combined organic phases are washed with sodium chloride solution, dried over sodium sulphate and concentrated to dryness. Column chromatography ($\phi$ 3 cm) on 50 g of silica gel (230–400 mesh) using petroleum ether/ethyl acetate (5:1) gives 1.0 g (51% of theory) of yellowish amorphous solid.

UV (MeOH): λ max.=304 nm.

EXAMPLE 23

Methyl erythro-(E)-7-[1-ethyl-5-(4-fluorophenyl)-7-isopropyl-3-methyl-2,4-dioxo-1,2,3,4-tetrahydro-pyrido-(2,3-d)pyrimidin-6-yl]-3,5-dihydroxy-hept-6-enoate

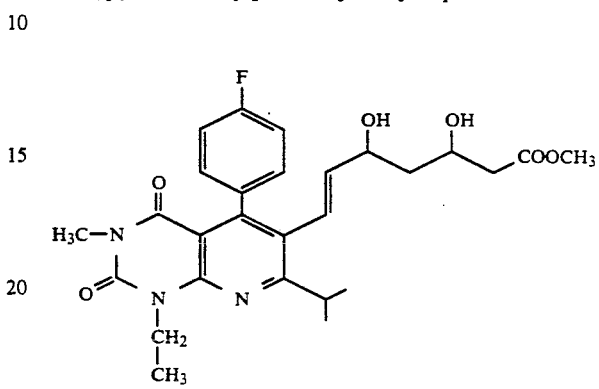

Analogously to the procedures for Example 7 and 8, 0.38 g (30% of theory) of the title compound is obtained as colorless crystals from 1.0 g (2.5 mmol) of the compound from Example 22.

m.p.: 123° C. from ether.

EXAMPLE 24

5-(4-Fluorophenyl)-7-isopropyl-6-methoxycarbonyl-2,4-dioxo-1,2,3,4,5,8-hexahydro-pyrido(2,3-d)pyrimidine

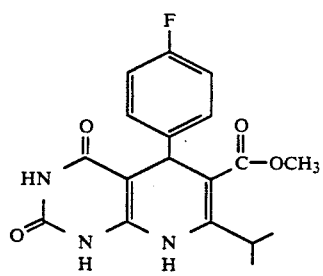

12.7 g (0.1 mol) of 6-amino-pyrimidine-2,4(1H, 3H)-dione and 50 g (0.2 mol) of the compound from Example 19 are stirred overnight at 140° C. in 500 ml of dimethylformamide. The mixture is filtered off hot from a little precipitate, poured onto 1 l of ice water and extracted three times with ethyl acetate. The organic phases are concentrated in vacuo and the residue is stirred thoroughly in methanol.

Yield: 22.8 g (64% of theory) of yellowish crystals.

m.p.: 274° C.

EXAMPLE 25

5-(4-fluorophenyl)-6-hydroxymethyl-7-isopropyl-2,4-dioxo-1,2,3,4-tetrahydro-pyrido(2,3-d)pyrimidine

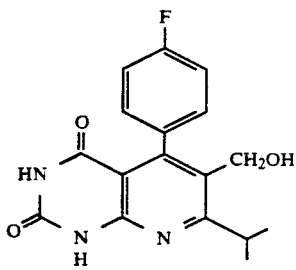

The title compound is prepared analogously to the procedure for Example 11 and Example 4, a total of 6.5 mol equivalents of diisobutylaluminum hydride being used in this case.

Yield: 1.4 g (20% of theory) of colorless crystals.
m.p.: 194° C. (semi-methoxide).

EXAMPLE 26

5-(4-Fluorophenyl)-6-formyl-7-isopropyl-2,4-dioxo-1,2,3,4-tetrahydro-pyrido(2,3-d)pyrimidine

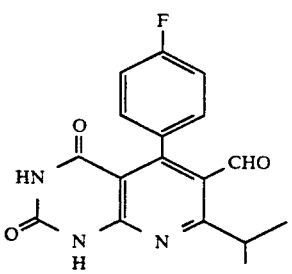

4.94 g (14.3 mmol) of the compound from Example 25, 3.1 g of neutral alumina and 6.45 g (30 mmol) of pyridinium chlorochromate are reacted analogously to Example 5.

Yield: 3.25 g (69% of theory) of yellowish solid.
m.p.: 232° C. (from ether).

EXAMPLE 27

(E)-3-[5-(4-Fluorophenyl)-7-isopropyl-2,4-dioxo-1,2,3,4-tetrahydro-pyrido(2,3-d)pyrimidin-6-yl]prop-2-enal

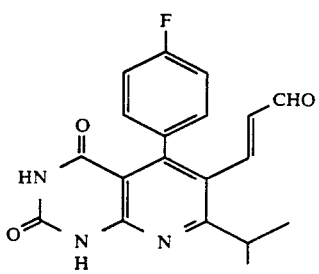

The title compound is prepared from 0.9 g (30 mmol) of 80% strength sodium hydride, 2.8 g (10.8 mmol) of diethyl 2-(cyclohexylamino)-vinyl-phosphonate and 2.95 g (9 mmol) of the compound from Example 26 analogously to the process of Example 6.

Yield: 1.0 g (31% of theory) of yellowish crystals.
m.p.: 255° C.

EXAMPLE 28

Methyl (E)-7-[5-(4-fluorophenyl)-7-isopropyl-2,4-dioxo-1,2,3,4-tetrahydro-pyrido(2,3-d)pyrimidin-6-yl]-5-hydroxy-3-oxo-hept-6-enoate

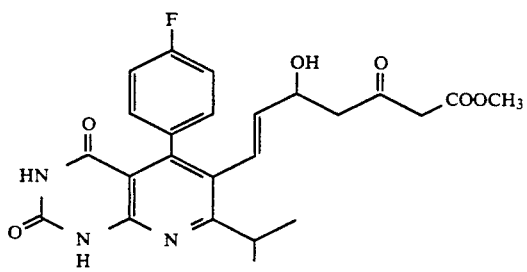

0.28 g (9.3 mmol) of 80% strength sodium hydride, 0.97 g (8.4 mmol) of methyl acetoacetate, 8.6 ml (14 mmol) of 15% strength butyllithium and 0.99 g (2.88 mmol) of the compound from Example 27 are reacted analogously to the procedure for Example 7.

Yield: 1.4 g of crude product.

EXAMPLE 29

Methyl erythro-(E)-7-[5-(4-fluorophenyl)-7-isopropyl-2,4-dioxo-1,2,3,4-tetrahydro-pyrido(2,3-d)pyrimidin-6-yl]-3,5-dihydroxy-hept-6-enoate

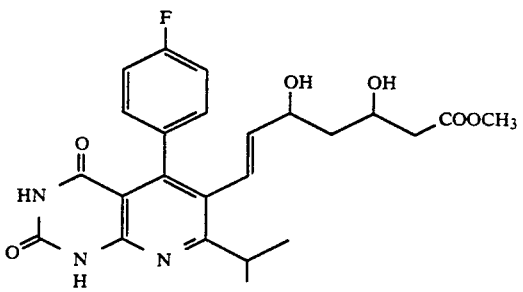

The title compound is obtained analogously to the procedure for Example 8 from 1.4 g (2.8 mmol) of the product from Example 28.

Yield: 190 mg (14% of theory) of colorless solid.
m.p.: 148° C.

The examples shown in Table 1 were prepared analogously to the procedure for Example 9 from the compounds of Examples 16, 18, 21, 23, 29, 44, 50 and 53.

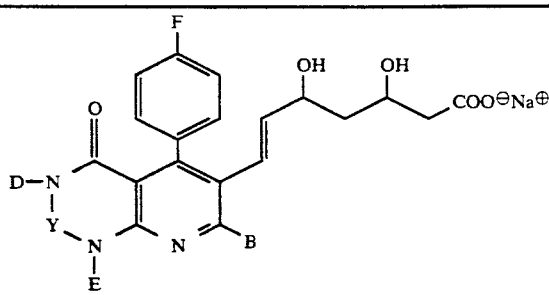

| Ex. | B | D | E | Y | m.p. (°C.) | FAB-MS |
|---|---|---|---|---|---|---|
| 30 | isopropyl | H | $CH_3$ | >=O | 179 (Decomp.) | 494 (M + H); 508 (M + Na) |
| 31 | isopropyl | H | $CH_3$ | >$CH_2$ | 183 (Decomp.) | 480 (M + H); 502 (M + Na) |
| 32 | isopropyl | H | $CH_2CH_3$ | >=O | 122 (Decomp.) | 508 (M + H); 530 (M + Na) |
| 33 | isopropyl | $CH_3$ | $CH_2CH_3$ | >=O | 117 (Decomp.) | 522 (M + H); 544 (M + Na) |
| 34 | isopropyl | H | H | >=O | 203 (Decomp.) | 480 (M + H); 502 (M + Na) |
| 35 | cyclopropyl | H | $-CH_2CH_3$ | >=O | 184° (Decomp.) | 506 (M + H); 528 (M + Na) |
| 36 | cyclopropyl | $CH_3$ | $-CH_2CH_3$ | >=O | 148° (Decomp.) | 520 (M + H); 542 (M + Na) |
| 37 | isopropyl | H | $-CH_2-$phenyl | >=O | amphorous | 570 (M + H); 592 (M + Na) |

EXAMPLE 38 trans-6-{2-[1-Ethyl-5-(4-fluorophenyl)-7-isopropyl-3-methyl-2,4-dioxo-1,2,3,4-tetrahydro-pyrido(2,3-d)pyrimidin-6-yl]-ethenyl}-4-hydroxy-3,4,5,6-tetrahydro-2H-pyran-2-one

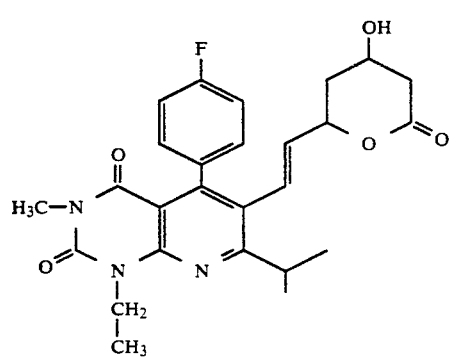

208 mg (0.4 mmol) of the compound from Example 33 are dissolved in 10 ml of water, 0.4 ml (0.4 mmol) of 1 N hydrochloric acid is added and it is extracted five times with dichloromethane. The combined organic phases are dried over magnesium sulphate and concentrated in vacuo, and the residue is boiled in 15 ml of toluene in a water separator for 18 h. After concentrating, the residue is chromatographed on 20 g of silica gel (230–400 mesh) in a column (diameter 2 cm) using petroleum ether/ethyl acetate (1:1).

Yield: 140 mg (73% of theory) of amorphous colorless solid.

$^1$H-NMR (CDCl$_3$): δ=1.25–1.7 (m, 11H, CH(CH$_3$)$_2$, CH$_2$-CH$_3$, O—CH—CH$_2$—C(OH)); 2.03 (d, 1H, OH); 2.5–2.7 (m, 2H, CH$_2$—C=O); 3.8 (s, 1H, N—CH$_3$); 3.9 (m, 1H, CH—(CH$_3$)$_2$); 4.2 (m, 1H, CH—O); 4.5 (q, 2H, N—CH$_2$); 5.1 (m, 1H, CH—O); 5.35 (dd, 1H, olefin-H); 6.3 (d, 1H, olefin-H); 6.95–7.15 (m, 4H, aromatic-H).

EXAMPLE 39

E,
Z-1-Cyclopropyl-3-(4-fluorophenyl)-2-methoxycarbonyl-prop-2-en-1-one

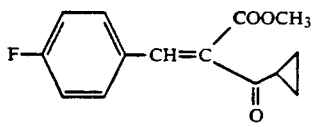

Analogously to Example 1, 43.2 g (87%) of the title compound of b.p. (140°–48° C./0.2 mbar) are obtained from 282.4 g (2 mol) of methyl 3-cyclopropyl-3-oxopropionate [W. F. Berkowitz, A. A. Ozorio, J. Org. Chem. 36, 3787–92 (1971)] and 260.4 g (2.1 mol) of 4-fluorobenzaldehyde.

EXAMPLE 40

(E)-3-[7-Cyclopropyl-1-ethyl-5-(4-fluorophenyl)-2,4-dioxo-1,2,3,4-tetrahydro-pyrido(2,3-d)pyrimidin-6-yl]-prop-2-enal

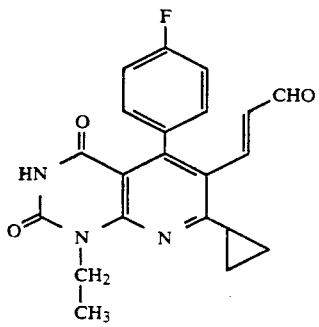

Starting from 6-amino-1-ethyl-uracil and the compound from Example 36, the title compound is prepared analogously to the procedures of Examples 24, 11, 4, 5 and 15.

Melting point: 236° C.

EXAMPLE 41

Methyl erythro-(E)-7-[7-cyclopropyl-1-ethyl-5-(4-fluorophenyl)-2,4-dioxo-1,2,3,4-tetrahydropyrido(2,3-d)pyrimidin-6-yl]-3,5-dihydroxy-hept-6-enoate

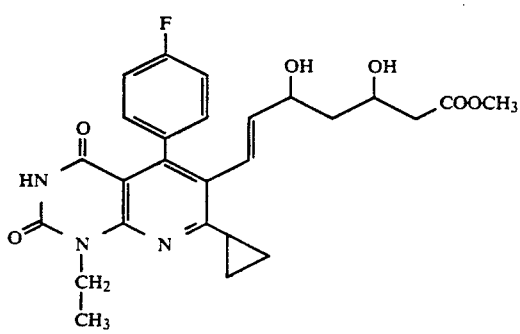

The title compound is obtained from the compound of Example 40 in analogy to the procedures of Examples 7 and 8.

Yield: 32% of theory, melting point 123° C. (dichloromethane), petroleum ether).

The compounds shown in Table 2 were prepared in analogy to the procedures of Examples 24, 11, 4 and 5 starting from the compounds of Examples 1 to 19:

TABLE 2

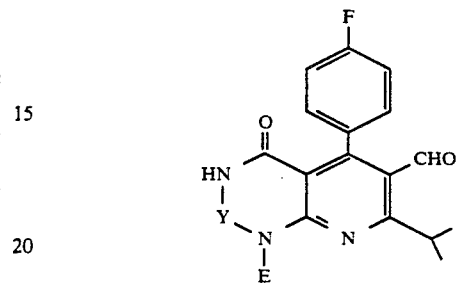

| Example No. | Y | E | m.p. (°C.) |
|---|---|---|---|
| 42 | >=< | phenyl | 253° C. |
| 43 | >=O | —(CH₂)₂CH₃ | 156° C. |
| 44 | >=< | —CH₂CH₃ | 217° C. |

EXAMPLE 45

E-3-[7-Cyclopropyl-1-ethyl-5(4)-fluorophenyl)-3-methyl-2,4-dioxo-1,2,3,4-tetrahydro-pyrido(2,3-d)pyrimidin-6-yl]prop-2-enal

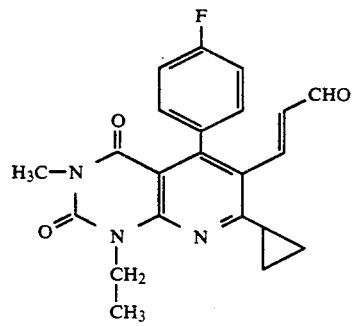

The compound is prepared from the compound of Example 40 analogously to the procedure for Example 22.

Yield: 56% of theory, melting point 147° C.

EXAMPLE 46

1-Allyl-5-(4-flouorophenyl)-6-formyl-7-isopropyl-2,4-dioxo-1,2,3,4-tetrahydro-pyrido(2,3-d)pyrimidine

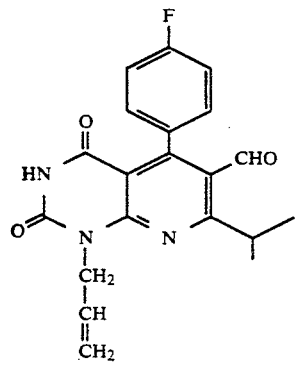

0.2 g (6.5 mmol) of 80% strength sodium hydride are added with ice cooling to a suspension of 2.13 g (6.5 mmol) of the compound from Example 26 in 20 ml of dimethylformamide. The mixture is stirred at room temperature for 10 min until everything has dissolved. 0.79 g (6.5 mmol) of allyl bromide are then added dropwise and the mixture is stirred at room temperature for 1 h. It is then poured onto 50 ml of ice water and the mixture is extracted twice with 50 ml of ethyl acetate. The organic phases are washed with saturated sodium chloride solution, then dried over sodium sulphate and concentrated. The residue is chromatographed on 60 g of silica gel (230–400 mesh), column diameter 4 cm using petroleum ether/ethyl acetate (2:1).

Yield: 0.95 g (40%) of colorless crystals of melting point 154° C. (from ether, petroleum ether).

EXAMPLE 47

5-(4-Fluorophenyl)-6-formyl-1,7-diisopropyl-2,4-dioxo-1,2,3,4-tetrahydro(2,3-d)pyrimidine

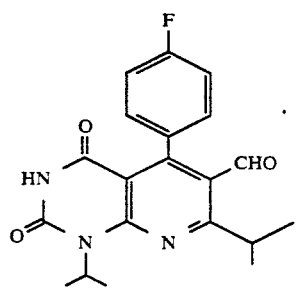

The compound is obtained from the compound of Example 26 and isopropyl iodide analogously to the process for Example 43, the mixture being kept at 50° C. for 18 h.

Yield: 36% of theory, melting point 197° c.

EXAMPLE 48

1-Benzyl-5-(4-fluorophenyl)-6-formyl-7-isopropyl-2,4-dioxo-1,2,3,4-tetrahydro(2,3-d)pyrimidine

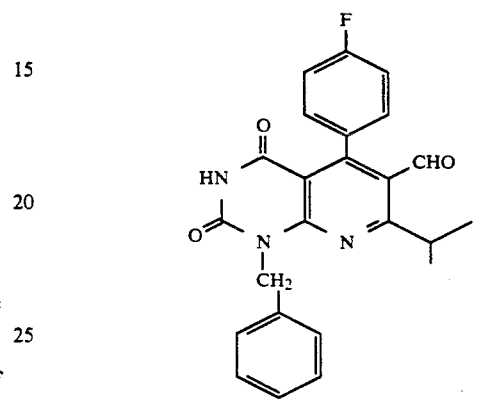

Analogously to the procedure of Example 46 from the compound of Example 26 and benzyl bromide.

Yield: 37% of theory, melting point 237° C.

EXAMPLE 49

1,3-Dibenzyl-5-(4-fluorophenyl)-6-formyl-7-isopropyl-2,4-dioxo-1,2,3,4-tetrahydro(2,3-d)pyrimidine

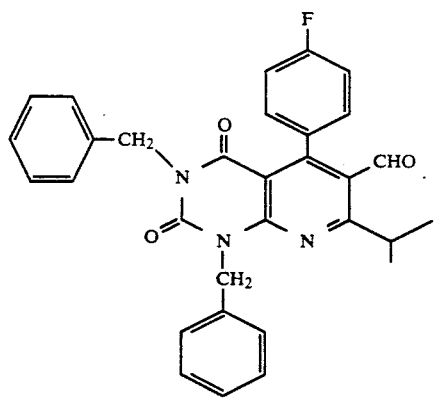

The compound is obtained in the preparation of Example 48 as a second product. It is isolated by silica gel chromatography using petroleum ether/ethyl acetate.

Yield: 24% of theory, amorphous colorless solid.

$^1$H-NMR (CDCl$_3$): δ=1.3 (d, 6H), 3.95 (hept. 1H), 5.13 (s, 2H), 5.67 (s, 2H), 7.15–7.5 (m, 14H), 9.6 (s, 1H).

The compounds shown in Table 3 were prepared in analogy to the procedures of Examples 7, 8 and 15.

TABLE 3

[Structure with substituents B, D, E, Y shown on a pyridine-fused ring system with 4-fluorophenyl, dihydroxy heptenoate methyl ester side chain]

| Ex. No. | B | D | E | Y | m.p. (°C.) |
|---|---|---|---|---|---|
| 50 | cyclopropyl | CH₃ | —C₂H₅ | >=O | amphorous |
| 51 | isopropyl | H | —CH₂—CH=CH₂ | >=O | 167 |
| 52 | isopropyl | H | isopropyl | >=O | 137 |
| 53 | isopropyl | H | —CH₂—C₆H₅ | >=O | 177 |
| 54 | isopropyl | CH₂—C₆H₅ | —CH₂—C₆H₅ | >=O | 82 |
| 55 | isopropyl | H | —C₆H₅ | >=O | 194 |
| 56 | isopropyl | H | —CH₂—CH₂—CH₃ | >=O | 153 |
| 57 | isopropyl | H | —C₂H₅ | >=S | amphorous* |

*In the preparation of Example 57, the reaction is not carried out using hydrogen peroxide, but the crude product is stirred for 3 h at room temperature in a 200-fold amount of methanol

EXAMPLE 58

Ethyl 4-fluorobenzoyl acetate

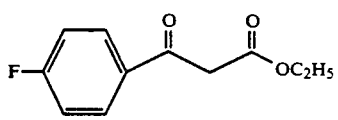

21.7 g (0.72 mol) of sodium hydride (80% strength, 20% mineral oil) are weighed into one liter of diethyl ether p.a. and 85.5 g (127 ml, 0.72 mol) of diethyl carbonate are then added. A solution of 100 g (0.72 mol) of 4-fluoroacetophenone in 300 ml of diethyl ether is added dropwise to this solution at boiling heat over a period of 4 hours (an efficient mechanical stirrer is necessary; a viscous suspension is formed). The mixture is then heated under reflux for a further hour, then cooled to about 5° C. and a solution of 50 ml of acetic acid and 100 ml of Et₂O is first added dropwise at this temperature under N₂. About 500 ml of H₂O is then added dropwise and the organic phase is separated off. The aqueous phase is extracted again with Et₂O (2×400 ml), and the combined ethereal phases are washed with NaHCO₃ solution, dried over MgSO₄ and concentrated. The residue is distilled through a short Vigreux column. Yield: 93 g (60%) b.p. 0.4 mm 99°–102° C.

EXAMPLE 59

Ethyl 2-(4-fluorobenzoyl)-4-methyl-pent-2-ene-carboxylate

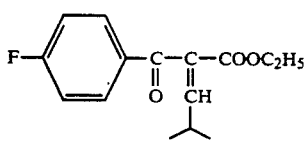

A solution of 210 g (1 mol) of ethyl 4-fluorobenzoyl acetate and 144 g (2 mol) of 2-methylpropanol are stirred overnight at 50° C. in 100 ml of isopropanol containing 7 ml of pyridine and 5 ml of acetic acid. After reduction is complete, the mixture is concentrated at about 15 Torr and the crude product (270 g ~85% of theory) is further reacted without further purification.

EXAMPLE 60

1-Ethyl-7-(4-fluorophenyl)-6-formyl-5-isopropyl-2,4-dioxo-1,2,3,4-tetrahydro(2,3-d)pyrimidine

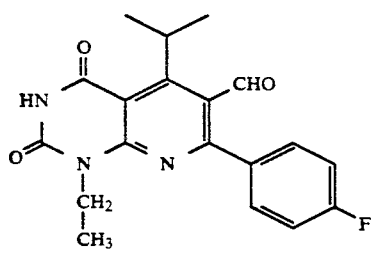

The title compound is prepared analogously to the reactions of Example 24, 3, 4 and 5 starting from the compound of Example 59 with 6-amino-1-ethyl-uracil.
Melting point: 216° C.

EXAMPLE 61

Methyl erythro-(E)-7[1-ethyl-7-(4-fluorophenyl-5-isopropyl-2,4-dioxo-1,2,3,4-tetrahydropyrido(2,3-d)pyrimidin-6-yl]-3,5-dihydroxy-hept-6-enoate

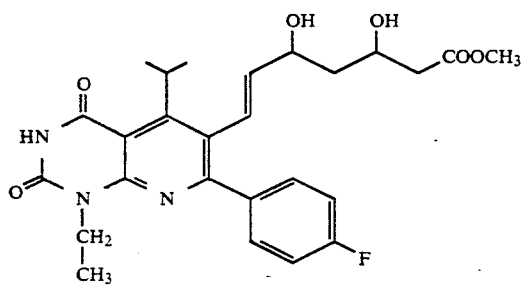

The title compound is obtained from the compound of Example 60 analogously to the procedures of Examples 7 and 8.
Yield: 30% of theory, melting point: 157° C.

EXAMPLE 62

The serum cholesterol-lowering action of the compounds according to the invention on the blood cholesterol values of dogs was discovered in feeding experiments of several weeks duration. For this purpose, the substance to be investigated was given together with the feed p.o. once daily in a capsule to healthy Beagle dogs over a period of several weeks. Cholestyramine (4 g/100 g of feed) as the gallic acid sequestrant was additionally mixed with the feed during the entire experimental period, i.e. before, during and after the administration period of the substance to be investigated.

Venous blood was taken from the dogs twice weekly and the serum cholesterol was determined enzymatically using a commercial test kit. The serum cholesterol values during the administration period were compared with the serum cholesterol values before the administration period (controls).

It is understood that the specification and examples are illustrative but not limitative of the present invention and that other embodiments within the spirit and scope of the invention will suggest themselves to those skilled in the art.

What is claimed is:

1. A substituted pyrido[2,3-d]pyrimidine of the formula (Ia) or (b)

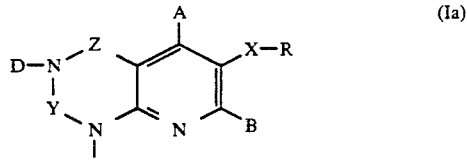

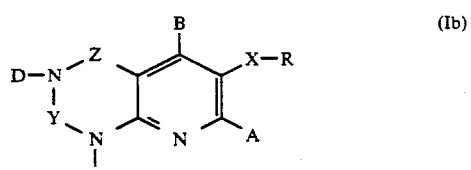

in which
A represents phenyl which is optionally monosubstituted to tetrasubstituted by identical or different straight-chain or branched substituents from the group consisting of alkyl, alkoxy and alkoxycarbonyl each having up to 8 carbon atoms, which may in turn be substituted by trifluoromethyl, hydroxyl, alkoxy having up to 4 carbon atoms, phenyl or phenoxy, or is substituted by phenyl, phenoxy, phenylthio, phenylsulphonyl, fluorine, chlorine, bromine, nitro, cyano, trifluoromethyl or phenyl which benzyloxy or
represents straight-chain or branched alkyl, each having up to 8 carbon atoms,
B represents cyclopropyl, cyclobutyl, cyclopentyl or cyclohexyl, or
represents trifluoromethyl or straight-chain or branched alkyl having up to 10 carbon atoms, which is optionally substituted by fluorine, chloride, bromine, hydroxyl, cyano, azido, trifluoromethyl, methylthio, methylsulphonyl, alkoxy having up to 6 carbon atoms or by phenyl, phenyloxy or phenylthio, where the phenyl radicals may be monosubstituted or disubstituted by identical or different substituents from the group consisting of fluorine, chlorine, bromine, cyano, trifluoromethyl, trifluoromethoxy, straight-chain or branched alkyl, alkoxy, alkylthio and alkylsulphonyl each having up to 6 carbon atoms, or
represents phenyl, which is optionally substituted by fluorine or chlorine
D represents hydrogen or
represents cyclopropyl, cyclobutyl, cyclopentyl or cyclohexyl, or
represents straight-chain or branched alkyl having up to 10 carbon atoms, which is optionally substituted by fluorine, chlorine, bromine, hydroxyl or alkoxy having up to 6 carbon atoms,
E has the meaning mentioned above for A and is identical or different, or
represents hydrogen or
represents cyclopropyl, cyclobutyl, cyclopentyl or cyclohexyl, or
represents straight-chain or branched alkyl having up to 10 carbon atoms, which is optionally substituted by fluorine, chlorine, bromine, straight-chain or branched alkyl having up to 6 carbon atoms, or phenyl, Y and Z are identical or different and represent a group of the formula

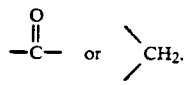

or

Y represents a thiocarbonyl group,
X represents a group of the formula —CH₂—CH₂— or —CH=CH— and
R represents a group of the formula

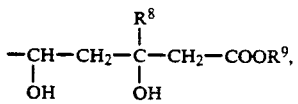

in which
R⁸ denotes hydrogen or straight-chain or branched alkyl having up to 8 carbon atoms, and
R⁹ denotes hydrogen or straight-chain or branched alkyl having up to 8 carbon atoms or benzyl, or denotes phenyl or a cation,
or pharmaceutically acceptable salts thereof.

2. A substituted pyrido[2,3-d]pyrimidines of the formula

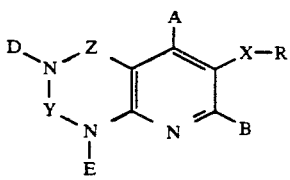

wherein
A represents phenyl, optionally, mono- or disubstituted by C₁-C₄-alkyl, phenoxy, fluorine or trifluoro-methyl, or represents straight or branched C₁-C₄-alkyl,
B represents phenyl, optionally mono- or disubstituted by fluorine, or
C₁-C₄-alkyl, or
cyclopropyl,
D represents hydrogen, or represents straight or branched C₁-C₄-alkyl,
E represents hydrogen, straight or branched C₁-C₄-alkyl or
phenyl, or benzyl,
Y represents the group

Z represents the group

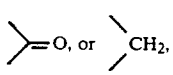

X represents —CH=CH—,
R represents a group of the formula

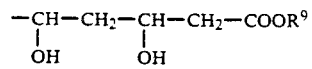

R⁹ represents hydrogen, a straight or branched C₁-C₄-alkyl, or denotes a sodium or potassium ion, or pharmaceutically accetable salts thereof.

3. A compound according to claim 1, wherein such compound is methyl erythro-(E)-7-[5-(4-fluorophenyl)-7-isopropyl-1-methyl-2,4-dioxo-1,2,3,4-tetrahydro-pyrido(2,3-d)pyrimidin-6-yl]-3,5-dihydroxy-hept-6-enoate of the formula

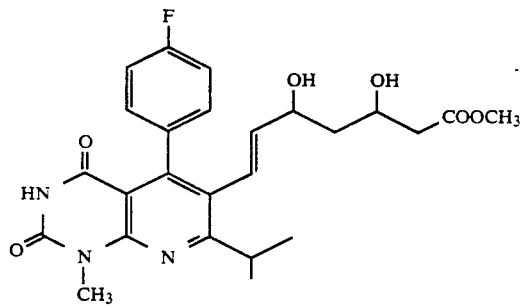

or a pharmaceutically acceptable salt thereof.

4. A compound according to claim 1, wherein such compound is methyl erythro-(E)-7-[1-ethyl-5-(4-fluorophenyl)-7-isopropyl-2,4-dioxo-1,2,3,4-tetrahydro-pyrido(2,3-d)pyrimidin-6-yl]-3,5-dihydroxy-hept-6-enoate of the formula

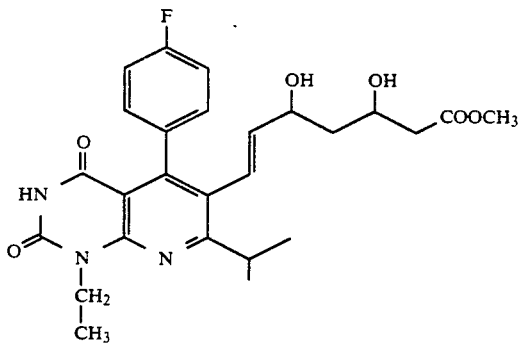

or a pharmaceutically acceptable salt thereof.

5. A compound according to claim 1, wherein such compound is methyl erythro-(E)-7-[5-(4-fluorophenyl)-7-isopropyl-2,4-dioxo-1,2,3,4-tetrahydro-pyrido(2,3-d)pyrimidin-6-yl]-3,5-dihydroxy-hept-6-enoate of the formula

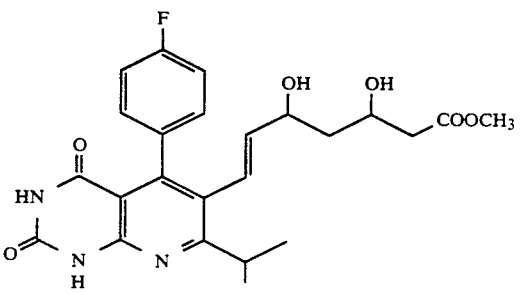

or a pharmaceutically acceptable salt thereof.

6. A compound according to claim 1, wherein such compound is 7-[5-fluorophenyl)-7-isopropyl-1-methyl-2,4-dioxo-1,2,3,4-tetrahydro-pyrido(2,3-d)-pyrimidin-6-yl]-3,5-dihydroxy-hept-6-enoic acid of the formula

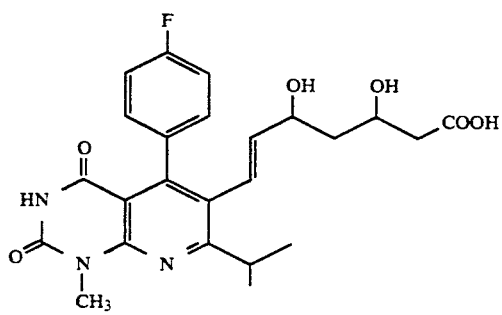

or a pharmaceutically acceptable salt thereof.

7. A compound according to claim 1 wherein such compound is 7-[5-(4-fluorophenyl)-7-isopropyl-1-ethyl-2,4-dioxo-1,2,3,4-tetrahydro-pyrido(2,3-d)-pyrimidin-6-yl]-3,5-dihydroxy-hept-6-enoic acid of the formula

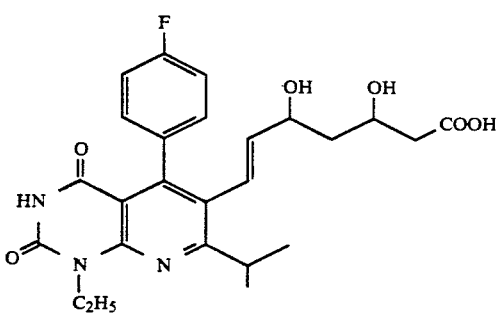

or a pharmaceutically acceptable salt thereof.

8. A compound according to claim 1, wherein such compound is 7-[5-(4-fluorophenyl)-7-isopropyl-1-benzyl-2,4-dioxo-1,2,3,4-tetrahydro-pyrido(2,3-d)-pyrimidin-6-yl]-3,5-dihydroxy-hept-6-enoic acid of the formula

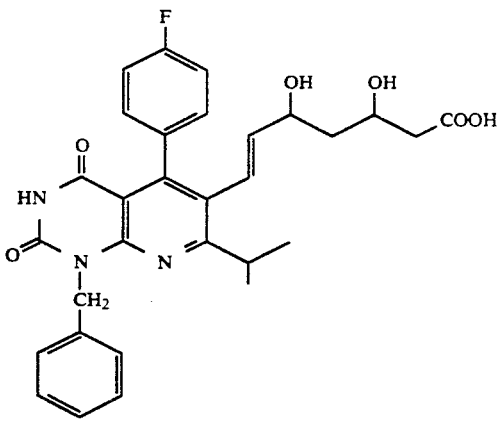

or a pharmaceutically acceptable salt thereof.

9. A compound according to claim 1, wherein such compound is methyl erythro-(E)-7-[7-cyclopropyl-1-ethyl-5-(4-fluorophenyl)-2,4-dioxo-1,2,3,4-tetrahydropyrido(2,3-d)pyrimidin-6-yl]-3,5-dihydroxy-hept-6-enoate of the formula

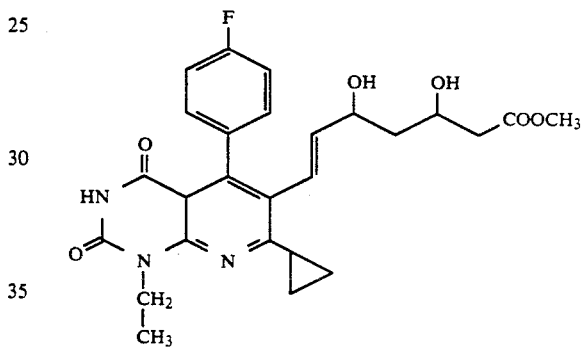

or a pharmaceutically acceptable salt thereof.

10. An HMG-CoA reductase inhibiting composition comprising an amount effective thereof of a compound of a pharmaceutically acceptable salt thereof according to claim 1 and a diluent.

11. A method of inhibiting HMG-CoA reductase in a patient in need thereof which comprises administering to such patient an amount effective therefor of a compound or pharmaceutically acceptable salt thereof according to claim 1.

12. The method according to claim 11, wherein such compound is
methyl erythro-(E)-7-[5-(4fluorophenyl)-7-isopropyl-1-methyl-2,4-dioxo-1,2,3,4-tetrahydro-pyrido(2,3-d)pyrimidin-6-yl]-3,5-dihydroxy-hept-6-enoate,
methyl erythro-(E)-7-[1-ethyl-5-(4-fluorophenyl)-7-isopropyl-2,4-dioxo-1,2,3,4-tetrahydro-pyrido(2,3-d)pyrimidin-6yl]-3,5-dihydroxy-hept-6-enoate,
methyl erythro-(E)-7-[5-(4-fluorophenyl)-7-isopropyl-2,4-dioxo-1,2,3,4-tetrahydro-pyrido(2,3-d)pyrimidin-6yl]-3,5-dihydroxy-hept-6-enoate,
7-[5-(4-fluorophenyl)-7-isopropyl-1-methyl-2,4-dioxo-1,2,3,4-tetrahydro-pyrido(2,3-d)-pyrimidin-6-yl]-3,5-dihydroxy-hept-6-enoic acid,
7-[5-(4-fluorophenyl)-7-isopropyl-1-ethyl-2,4-dioxo-1,2,3,4-tetrahydro-pyrido(2,3-d)-pyrimidin-6-yl]-3,5-dihydroxy-hept-6-enoic acid,
7-[5-(4-fluorophenyl)-7-isopropyl-1-benzyl-s,4-dioxo-1,2,3,4-tetrahydro-pyrido(2,3-d)-pyrimidin-6-yl]-3,5-dihydroxy-hept-6-enoic acid, or
methyl erythro-(E)-7-[7-cyclopropyl-1-ethyl-5-(4-fluorophenyl)-2,4-dioxo-1,2,3,4-tetrahydro-pyrido(2,3-d)pyrimidin-6-yl]-3,5-dihydroxy-hept-6-enoate,
or a pharmaceutically acceptable salt thereof.

* * * * *

UNITED STATES PATENT AND TRADEMARK OFFICE
CERTIFICATE OF CORRECTION

PATENT NO.  : 5,075,311

DATED       : December 24, 1991

INVENTOR(S) : Hubsch et al.

It is certified that error appears in the above-identified patent and that said Letters Patent is hereby corrected as shown below:

| | |
|---|---|
| Title Page | [54] Title: Delete " PRYIDO " and substitute -- PYRIDO -- |
| Title Page | U.S. PATENT DOCUMENTS: After " 4,613,610, 9/1986, Wareing,..... " delete " 54 " and substitute -- 514 -- |
| Title Page | FOREIGN PATENT DOCUMENTS: After " 0022478, 2/1983, delete " European Pat. Off. and substitute -- Fed. Rep. of Germany -- |
| Col. 1, line 2 | Title: Delete " PRYIDO " and substitute -- PYRIDO -- |
| Col. 50, line 28 | After 2nd " or " insert -- phenyl which -- |
| Col. 50, lines 30 31 | Delete " phenyl which " |
| Col. 50, line 67 | Delete " alkyl " and substitute -- alkenyl -- |

UNITED STATES PATENT AND TRADEMARK OFFICE
CERTIFICATE OF CORRECTION

PATENT NO. : 5,075,311

DATED : December 24, 1991

INVENTOR(S) : Hubsch et al.

It is certified that error appears in the above-indentified patent and that said Letters Patent is hereby corrected as shown below:

Col. 54, line 40    Delete " thereof " and substitute -- therefor --

Signed and Sealed this

Second Day of November, 1993

Attest:

BRUCE LEHMAN

Attesting Officer

Commissioner of Patents and Trademarks